(12) United States Patent
Shikii et al.

(10) Patent No.: US 11,046,179 B2
(45) Date of Patent: Jun. 29, 2021

(54) WAKEFULNESS INDUCTION CONTROL DEVICE AND WAKEFULNESS INDUCTION SYSTEM

(71) Applicant: Panasonic Intellectual Property Management Co., Ltd., Osaka (JP)

(72) Inventors: Shinichi Shikii, Nara (JP); Koichi Kusukame, Nara (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/615,793

(22) PCT Filed: May 22, 2018

(86) PCT No.: PCT/JP2018/019564
§ 371 (c)(1),
(2) Date: Nov. 21, 2019

(87) PCT Pub. No.: WO2018/216669
PCT Pub. Date: Nov. 29, 2018

(65) Prior Publication Data
US 2020/0189389 A1      Jun. 18, 2020

(30) Foreign Application Priority Data

May 25, 2017   (JP) .............. JP2017-103290

(51) Int. Cl.
*B60K 28/06* (2006.01)
*B60W 40/08* (2012.01)
(Continued)

(52) U.S. Cl.
CPC ............. *B60K 28/06* (2013.01); *B60W 40/08* (2013.01); *G06K 9/00845* (2013.01); *G08B 21/06* (2013.01); *B60W 2040/0827* (2013.01)

(58) Field of Classification Search
None
See application file for complete search history.

(56) References Cited

U.S. PATENT DOCUMENTS 7,710,279 B1 * 5/2010 Fields .................... G08B 21/06
                                                            340/309.16
9,118,775 B2 * 8/2015 Lim ........................ H04W 4/12
(Continued)

FOREIGN PATENT DOCUMENTS

JP    H11-109985 A    4/1999
JP    H11-310053 A    11/1999
(Continued)

OTHER PUBLICATIONS

International Search Report issued in corresponding International Patent Application No. PCT/JP2018/019564, dated Jul. 17, 2018, with English translation.

*Primary Examiner* — Thomas S McCormack
(74) *Attorney, Agent, or Firm* — McDermott Will & Emery LLP

(57) ABSTRACT

A wakefulness induction control device includes a sleepiness detector that detects a sleepiness level indicating a degree of sleepiness of a user; a controller that actuates a wakefulness inducer that induces wakefulness in the user when the sleepiness level detected by the sleepiness detector meets a predetermined reference, and stops the wakefulness inducer when a predetermined duration has passed after actuation of the wakefulness inducer, and an output that outputs actuating information of the wakefulness inducer. The actuating information includes time information indicating the duration left until the controller stops the wakefulness inducer.

60 Claims, 13 Drawing Sheets

(51) Int. Cl.
*G06K 9/00* (2006.01)
*G08B 21/06* (2006.01)

(56) References Cited

U.S. PATENT DOCUMENTS

| | | | |
|---|---|---|---|
| 2004/0044293 A1* | 3/2004 | Burton | B60L 3/02 |
| | | | 600/544 |
| 2015/0105976 A1 | 4/2015 | Shikii et al. | |
| 2016/0374606 A1 | 12/2016 | Shikii et al. | |
| 2017/0020432 A1 | 1/2017 | Kusukame et al. | |
| 2017/0102783 A1 | 4/2017 | Shikii et al. | |
| 2017/0150930 A1 | 6/2017 | Shikii et al. | |
| 2018/0244288 A1* | 8/2018 | Glaser | B60W 50/14 |
| 2019/0299744 A1 | 10/2019 | Kusukame et al. | |

FOREIGN PATENT DOCUMENTS

| | | |
|---|---|---|
| JP | 2005-186657 A | 7/2005 |
| JP | 2009-31905 A | 2/2009 |
| JP | 2010-133692 A | 6/2010 |
| JP | 2010-186276 A | 8/2010 |
| JP | 2015-18517 A | 1/2015 |
| JP | 2015-096413 A | 5/2015 |
| JP | 2017-012730 A | 1/2017 |
| JP | 2017-73107 A | 4/2017 |
| JP | 2017-099846 A | 6/2017 |
| JP | 2017-127616 A | 7/2017 |
| JP | 2019-006363 A | 1/2019 |
| JP | 2019-067385 A | 4/2019 |
| WO | 2019/065749 A1 | 4/2017 |
| WO | 2018/105331 A1 | 6/2018 |
| WO | 2019/065765 A1 | 4/2019 |

\* cited by examiner

FIG. 3

| SLEEPINESS LEVEL | 1 | 2 | 3 | 4 | 5 |
|---|---|---|---|---|---|
| DEGREE OF SLEEPINESS | NOT SLEEPY | ... | SLEEPY | ... | VERY SLEEPY |
| CHARACTERISTICS EXAMPLE | - BLINK AT STABLE CYCLES<br>- LINE OF SIGHT CHANGES RAPIDLY<br>- LINE OF SIGHT CHANGES FREQUENTLY | - LINE OF SIGHT CHANGES SLOWLY<br>- LIPS BECOME PARTED | - BLINK SLOWLY<br>- BLINK AT SHORT CYCLES<br>- SECONDARY ACTION OCCURS WHEN BLINKING | - BLINK AT UNSTABLE CYCLES<br>- YAWN | - EYELIDS CLOSE<br>- HEAD TILTS FORWARD |

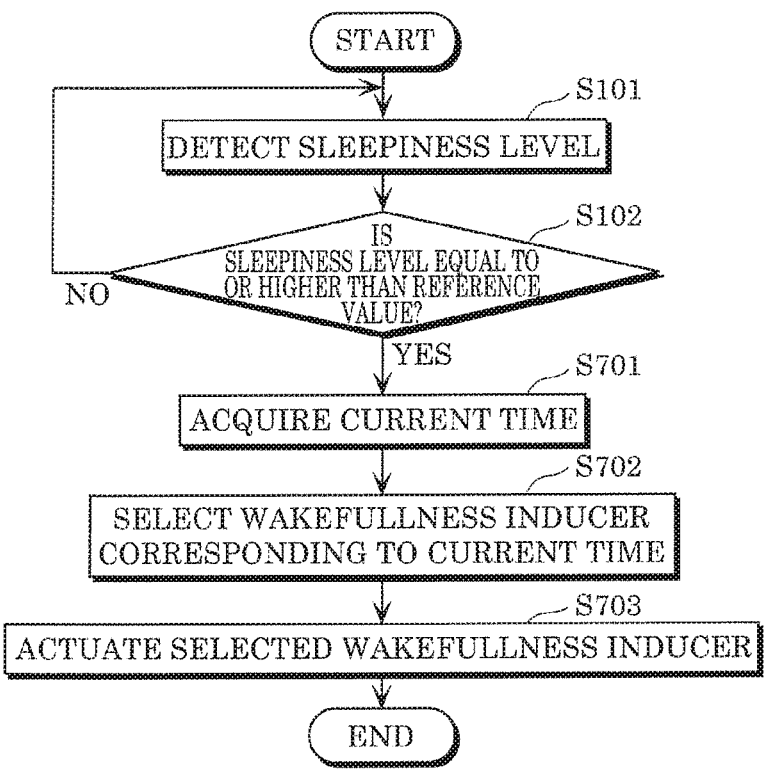
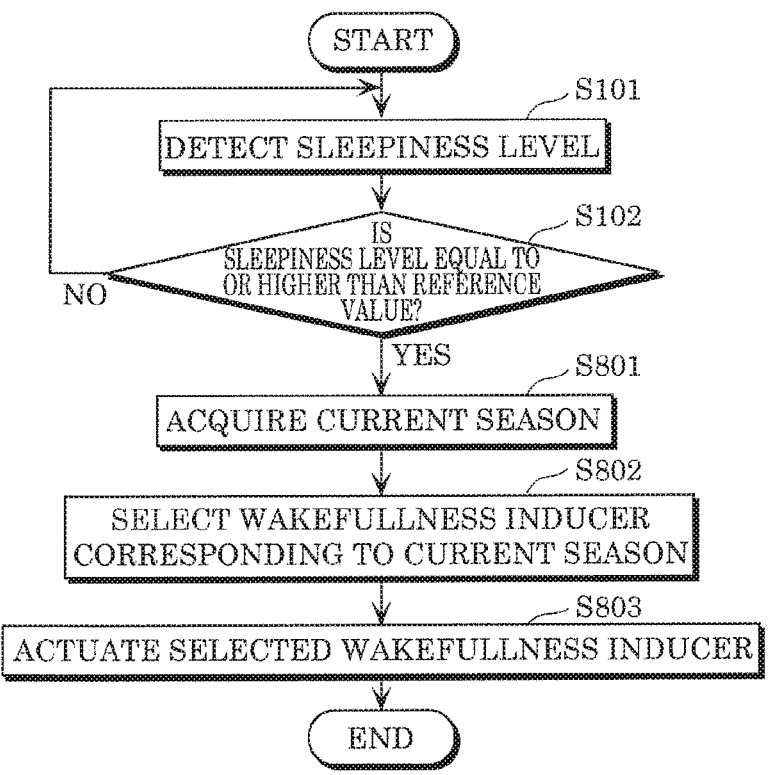

WAKEFULNESS INDUCTION CONTROL DEVICE AND WAKEFULNESS INDUCTION SYSTEM

CROSS-REFERENCE OF RELATED APPLICATIONS

This application is the U.S. National Phase under 35 U.S.C. § 371 of International Patent Application No. PCT/JP2018/019564, filed on May 22, 2018, which in turn claims the benefit of Japanese Patent Application No. 2017-103290, filed on May 25, 2017, the entire disclosures of which Applications are incorporated by reference herein.

TECHNICAL FIELD

The present disclosure relates to a wakefulness induction control device and a wakefulness induction system.

BACKGROUND ART

To date, there is proposed a wakefulness induction control device that induces wakefulness in a person to shake off his/her sleepiness. For example, PTL 1 discloses a device that stimulates a person with heat by controlling the air conditioning to induce wakefulness in that person. In addition, for example, PTL 2 and PTL 3 disclose a device that stimulates a person with a sound by controlling the sound to induce wakefulness in that person. Furthermore, PTL 4 discloses a device that stimulates a person with a scent by controlling equipment that produces the scent to induce wakefulness in that person.

CITATION LIST

Patent Literature

PTL 1: Japanese Unexamined Patent Application Publication No. 2005-186657
PTL 2: Japanese Unexamined Patent Application Publication No. 2009-31905
PTL 3: Japanese Unexamined Patent Application Publication No. 11-109985
PTL 4: Japanese Unexamined Patent Application Publication No. 11-310053

SUMMARY OF THE INVENTION

Technical Problem

However, with an existing wakefulness induction control device that induces wakefulness in a person, its continuous use to induce wakefulness in a person may make the person become accustomed thereto. Therefore, the existing wakefulness induction control device suffers from shortcomings in that the effect of inducing wakefulness in a person (wakefulness inducing effect) decreases through its continuous use.

The present disclosure has been made to overcome such shortcomings and is directed to providing a wakefulness induction control device and so on that can keep the wakefulness inducing effect from decreasing by making it less likely for a user to become accustomed thereto.

Solutions to Problem

To overcome the foregoing shortcomings, a wakefulness induction control device according to one aspect of the present disclosure comprises a sleepiness detector that detects a sleepiness level indicating a degree of sleepiness of a person; a controller that actuates a wakefulness inducer that induces wakefulness in the person when the sleepiness level detected by the sleepiness detector meets a predetermined reference, and stops the wakefulness inducer when a predetermined duration has passed after actuation of the wakefulness inducer; and an output that outputs actuating information of the wakefulness inducer, wherein the actuating information includes time information indicating a duration left until the controller stops the wakefulness inducer.

In addition, a wakefulness induction system according to one aspect of the present disclosure comprises the above wakefulness induction control device and the above wakefulness inducer.

Advantageous Effect of Invention

The wakefulness induction control device and so on according to the present disclosure can keep the wakefulness inducing effect from decreasing.

BRIEF DESCRIPTION OF DRAWINGS

FIG. 3 illustrates an example of a person's characteristics corresponding to his/her sleepiness level.

FIG. 13 is a flowchart illustrating a first example of a procedure through which a wakefulness induction control device according to an embodiment selects a wakefulness inducer to be actuated.

FIG. 14 is a flowchart illustrating a second example of a procedure through which a wakefulness induction control device according to an embodiment selects a wakefulness inducer to be actuated.

Figure 1:
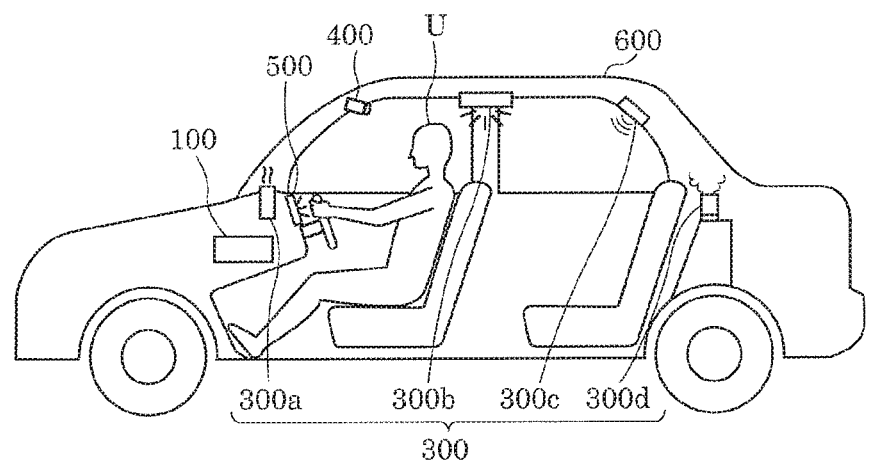
FIG. 1 is an illustration for describing an example of a system including a wakefulness induction control device according to an embodiment.

DESCRIPTION OF EXEMPLARY EMBODIMENTS (Overview of the Present Disclosure)

To overcome the above-described shortcomings, a wakefulness induction control device according to one aspect of the present disclosure includes a sleepiness detector that detects a sleepiness level indicating a degree of sleepiness of a person; and a controller that actuates a wakefulness inducer that induces wakefulness in the person when the sleepiness level detected by the sleepiness detector meets a predetermined reference, and stops the wakefulness inducer when a predetermined duration has passed after actuation of the wakefulness inducer.

With this configuration, the controller automatically stops the wakefulness inducer when the predetermined duration has passed. Therefore, a user (person) of the wakefulness induction control device is less likely to become accustomed to a method of inducing wakefulness even when the user has repeatedly used the wakefulness induction control device. In other words, the wakefulness induction control device according to the present disclosure can suppress a decrease in the wakefulness inducing effect on the user by making the user less likely to become accustomed to the wakefulness inducing method.

For example, the wakefulness induction control device may further include an output that outputs actuating information of the wakefulness inducer.

With this configuration, the wakefulness induction control device, upon being connected to a device such as a display or a speaker, can present the actuating information of the wakefulness inducer. Therefore, the user can more easily check the actuating information of the wakefulness inducer through the device such as a display or a speaker.

For example, the actuating information may include time information indicating a duration left until the controller stops the wakefulness inducer.

With this configuration, the user can check the duration left until the wakefulness inducer stops. Thus, when the wakefulness induction control device is installed, for example, in a vehicle, the user can make a plan, in accordance with the stated time, for securing a place to take a rest in time for the wakefulness inducer to stop. Accordingly, this configuration improves the usability of the wakefulness induction control device.

For example, the actuating information may include stop information that, when the controller has stopped the wakefulness inducer, indicates that the wakefulness inducer has been stopped.

With this configuration, the wakefulness induction control device can reduce any possibility that the user mistakenly thinks that the wakefulness inducer has stopped due to a failure or the like.

For example, the controller may change the predetermined duration in accordance with a current time.

With this configuration, the actuating duration of the wakefulness inducer is adjusted, for example, in accordance with the time that is estimated to be when the user is likely to feel sleepy, such as around an early afternoon. Accordingly, this configuration can increase the wakefulness inducing effect on the user.

For example, the controller may change the predetermined duration in accordance with the number of times the wakefulness inducer has been actuated.

This configuration can make the user less likely to become accustomed to the wakefulness inducing method of the wakefulness inducer. Accordingly, this configuration suppresses a decrease in the wakefulness inducing effect on the user.

For example, the wakefulness induction control device may be installed in a vehicle, and the controller may change the predetermined duration in accordance with a duration for which the person driving the vehicle has continuously driven the vehicle.

With this configuration, the controller can actuate the wakefulness inducer in consideration of how likely the user has become accustomed to the wakefulness inducing method of the wakefulness inducer in accordance with the driving duration of the user. Accordingly, this configuration further suppresses a decrease in the wakefulness inducing effect on the user.

For example, the controller may change the predetermined duration in accordance with a day's total driving duration of the person driving the vehicle.

With this configuration, the controller can actuate the wakefulness inducer in consideration of how likely the user has become accustomed to the wakefulness inducing method of the wakefulness inducer in accordance with the day's total driving duration of the user. Accordingly, this configuration further suppresses a decrease in the wakefulness inducing effect on the user.

For example, the wakefulness induction control device may be connected to a plurality of the wakefulness inducers that differ in a wakefulness inducing method of inducing wakefulness in the person, and the controller may stop each of the plurality of wakefulness inducers when the predetermined duration set differently for each of the plurality of wakefulness inducers has passed after actuation of the plurality of wakefulness inducers.

With this configuration, the wakefulness induction control device can make the user even less likely to become accustomed to the wakefulness inducing method in accordance with the wakefulness inducing method. Accordingly, this configuration further suppresses a decrease in the wakefulness inducing effect on the user.

For example, the controller may actuate one or more wakefulness inducers of the plurality of wakefulness inducers, stop the one or more wakefulness inducers, one by one, when the predetermined duration set differently for each of the plurality of wakefulness inducers has passed, and further actuate one or more wakefulness inducers of the plurality of wakefulness inducers different from the one or more wakefulness inducers that have been stopped.

This configuration can keep the same wakefulness inducer of the plurality of wakefulness inducers from being actuated continuously, and the number of times each wakefulness inducer is actuated is kept from becoming uneven. Therefore, the user is less likely to become accustomed to the wakefulness inducing method of each wakefulness inducer. In other words, this configuration further suppresses a decrease in the wakefulness inducing effect on the user.

For example, the controller may select one or more wakefulness inducers of the plurality of wakefulness inducers in accordance with a current time and actuate the one or more wakefulness inducers.

With this configuration, the wakefulness inducer may be actuated in accordance with an environment in which the user is estimated to use the wakefulness induction control device based on the current time. Accordingly, this configuration can increase the wakefulness inducing effect on the user.

For example, the controller may select one or more wakefulness inducers of the plurality of wakefulness inducers in accordance with a season and actuate the one or more wakefulness inducers.

With this configuration, a wakefulness inducer may be actuated that is suitable for the season and that can induce wakefulness in the user with high energy efficiency. Accordingly, this configuration can increase the wakefulness inducing effect on the user.

For example, the controller may randomly select one or more wakefulness inducers of the plurality of wakefulness inducers and actuate the one or more wakefulness inducers.

This configuration makes it more likely to keep the same wakefulness inducer of the plurality of wakefulness inducers from being actuated continuously. Therefore, the user is less likely to become accustomed to the wakefulness inducing method of each wakefulness inducer. In other words, this configuration further suppresses a decrease in the wakefulness inducing effect on the user.

For example, the controller may select one or more wakefulness inducers of the plurality of wakefulness inducers in accordance with an attribute of the person and actuate the one or more wakefulness inducers. The attribute of the user is information such as the age, the gender, or the physique of the user.

This configuration makes it possible to effectively induce wakefulness in the user in accordance with the attribute of the user.

For example, the wakefulness induction control device may further include a storage that stores, for each of the plurality of wakefulness inducers, an amount of change in the sleepiness level of the person in a direction of increasing wakefulness of the person with respect to the predetermined duration, and the controller may actuate one or more wakefulness inducers including a wakefulness inducer of which the amount of change stored in the storage is largest.

This configuration makes it possible to effectively induce wakefulness in the user in accordance with the characteristics of the user.

For example, the controller may determine an accustomedness level indicating a level of accustomedness of the person to the wakefulness inducer and change the method of actuating the wakefulness inducer based on the accustomedness level determined of the person.

With this configuration, when the controller has determined that the user has become accustomed to the wakefulness inducing method of the wakefulness inducer, the controller changes the wakefulness inducing method. Accordingly, a decrease in the wakefulness inducing effect on the user is further suppressed.

In addition, a wakefulness induction system according to one aspect of the present disclosure includes the above wakefulness induction control device and the above wakefulness inducer.

Thus, with the wakefulness induction system according to the present disclosure, the wakefulness inducer is stopped automatically when the preset predetermined duration has passed. Therefore, the user of the wakefulness induction system can use the wakefulness induction control device repeatedly without becoming accustomed to the method of inducing wakefulness. In other words, with the wakefulness induction system according to the present disclosure, the user can be made less likely to become accustomed to the wakefulness inducing method. Accordingly, a decrease in the wakefulness inducing effect on the user is suppressed.

Hereinafter, embodiments of the present disclosure will be described with reference to the drawings. The embodiments described below merely illustrate general or specific examples of the present disclosure. Therefore, the numerical values, the constituent elements, the arrangement and the connection modes of the constituent elements, the processes (steps), the order of the processes, and so on illustrated in the following embodiments are examples and are not intended to limit the present disclosure. Accordingly, among the constituent elements in the following embodiments, any constituent element that is not described in an independent claim expressing the broadest concept of the present disclosure will be described as an optional constituent element.

In addition, the drawings are schematic diagrams and do not necessarily provide the exact depictions. Therefore, the scales and so on do not necessarily match among the drawings. In the drawings, substantially identical configurations are given identical reference characters, and duplicate descriptions thereof will be omitted or simplified.

Embodiments

[Configuration]

First, a configuration of a wakefulness induction control device and a wakefulness induction system according to an embodiment will be described with reference to FIGS. 1 and 2.

FIG. 1 is an illustration for describing an example of a system including a wakefulness induction control device according to an embodiment. FIG. 2 is a block diagram illustrating a characteristic functional configuration of the wakefulness induction control device according to the embodiment.

Wakefulness induction control device 100 is provided in vehicle 600 illustrated in FIG. 1 and induces wakefulness in user U, such as a driver of vehicle 600.

Figure 2:
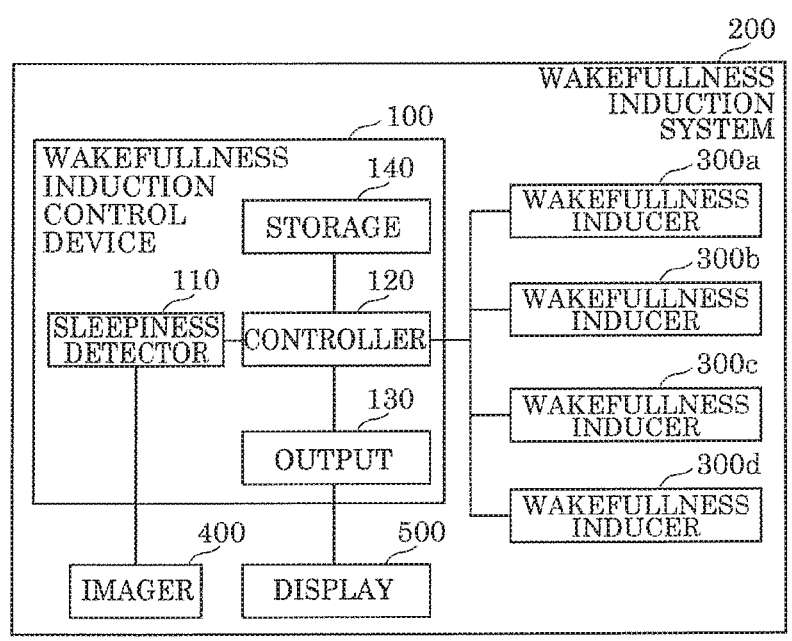
FIG. 2 is a block diagram illustrating a characteristic functional configuration of a wakefulness induction control device according to an embodiment.

As illustrated in FIG. 2, wakefulness induction control device 100 includes sleepiness detector 110, controller 120, output 130, and storage 140.

Sleepiness detector 110 detects a sleepiness level indicating the degree of sleepiness of user U. To rephrase, sleepiness detector 110 detects a wakefulness level indicating the degree of wakefulness of user U. For example, sleepiness detector 110 detects the sleepiness level of user U based on a moving image that includes user U captured by imager 400 connected to sleepiness detector 110. There is no particular limitation on the method of detecting the sleepiness level of user U, and the sleepiness level can be detected, for example, based on moving image information of the face of user U.

FIG. 3 illustrates an example of characteristics of user U corresponding to his/her sleepiness level.

As illustrated in FIG. 3, for example, when user U blinks at stable cycles, the sleepiness level is low and is determined to be 1, for example. When user U blinks slowly and frequently at short cycles, the sleepiness level is high and is determined to be 3, for example. In other words, user U is determined not to be sleepy when user U blinks at stable cycles and is determined to be sleepy when user U blinks slowly and frequently. In this manner, sleepiness detector 110 detects the sleepiness level of user U by analyzing a moving image that includes user U captured by imager 400.

The relationship among the sleepiness level, the degree of sleepiness, and the characteristics examples illustrated in FIG. 3 is merely an example, and this is not a limiting example. For example, the sleepiness level may be classified into six or more levels or into four or less levels.

In addition, as the degree of sleepiness of user U is higher, the numerical value of the sleepiness level may be set lower. In the following description, that the sleepiness level is low means that the degree of sleepiness of the user is low.

Examples of imager 400 include a camera including a complementary metal oxide semiconductor (CMOS) image sensor and a camera including a charge coupled device (CCD) image sensor.

Referring back to FIG. 2, when the sleepiness level detected by sleepiness detector 110 meets a predetermined reference, controller 120 actuates (i.e., starts actuating) one or more of wakefulness inducers 300a to 300d that each induce wakefulness in user U. For example, when the sleepiness level detected by sleepiness detector 110 is equal to or higher than a preset reference value of the sleepiness level, controller 120 actuates one or more of wakefulness inducers 300a to 300d that each induce wakefulness in user U. In the following description, wakefulness inducers 300a to 300d are collectively referred to as wakefulness inducer(s) 300. Wakefulness induction control device 100 is connected to one or more wakefulness inducers 300 via a wire (not illustrated) or the like.

Wakefulness inducers 300 are devices used to induce wakefulness in user U to lower the sleepiness level of user U. Examples of wakefulness inducers 300 include an acoustic device that emits a sound, an emission device that emits light, an aroma generator that produces a scent, and an air conditioner that controls the air conditioning, such as the temperature, the humidity, or the $CO_2$ concentration. In other words, wakefulness inducers 300 are devices that induce wakefulness by stimulating user U with a sound, light, heat, or the like or devices that lower the humidity, the $CO_2$ concentration, or the like to improve the environment causing the sleepiness in user U.

It suffices that the predetermined reference (reference value) be preset, and there is no particular limitation on the sleepiness level. For example, the reference value indicating that the sleepiness level is 3 may be prestored in storage 140.

Controller 120 actuates wakefulness inducer 300 when the sleepiness level detected by sleepiness detector 110 meets the predetermined reference and stops wakefulness inducer 300 when a predetermined duration has passed after actuation of wakefulness inducer 300. In other words, controller 120 actuates wakefulness inducer 300 when the sleepiness level detected by sleepiness detector 110 is equal to or higher than the reference value and stops actuating wakefulness inducer 300 when a predetermined duration has passed after actuation of wakefulness inducer 300.

Any desired preset duration may be used as the predetermined duration, and there is no particular limitation on the predetermined duration. For example, the predetermined duration may be preset to 5 minutes, 10 minutes, 15 minutes, or the like.

Controller 120 may change the predetermined duration in accordance with the current time. In addition, controller 120 may change the predetermined duration in accordance with the number of times wakefulness inducer 300 has been actuated, for example.

When wakefulness induction control device 100 is installed in vehicle 600, controller 120 may change the predetermined duration in accordance with the duration that the driver (user U) driving vehicle 600 has continuously driven. In this case, controller 120 may change the predetermined duration in accordance with the day's total driving duration that user U driving vehicle 600 has driven.

The reference based on which the sleepiness level is determined and the reference value of the sleepiness level may be set as desired, and there is no particular limitation.

When wakefulness induction control device 100 includes a plurality of wakefulness inducers 300 that differ in the wakefulness inducing method, controller 120 may stop each of one or more wakefulness inducers 300 of the plurality of wakefulness inducers 300, one by one, after respectively predetermined durations have passed after actuation of respective wakefulness inducers 300.

In addition, when wakefulness induction control device 100 includes a plurality of wakefulness inducers 300 that differ in the wakefulness inducing method, controller 120 may successively actuate each wakefulness inducer 300, one by one, of the plurality of wakefulness inducers 300. In this case, controller 120 may actuate one or more wakefulness inducers 300 different from one or more wakefulness inducers 300 actuated in a previous instance. In other words, controller 120 may actuate one or more wakefulness inducers 300 of the plurality of wakefulness inducers 300 and stop one or more wakefulness inducers 300, one by one, when the predetermined duration set differently for each wakefulness inducer 300 has passed. Furthermore, controller 120 may actuate one or more wakefulness inducers 300 of wakefulness inducers 300 different from one or more wakefulness inducers 300 that have been stopped.

There is no particular limitation on the method of selecting wakefulness inducer 300 to be actuated by controller 120 from the plurality of wakefulness inducers 300. For example, controller 120 may randomly select one or more wakefulness inducers 300 from the plurality of wakefulness inducers 300 and actuate selected one or more wakefulness inducers 300. In addition, for example, controller 120 may select one or more wakefulness inducers 300 from the plurality of wakefulness inducers 300 in accordance with the current time and actuate selected one or more wakefulness inducers 300. In addition, for example, controller 120 may select one or more wakefulness inducers 300 from the plurality of wakefulness inducers 300 in accordance with the season and actuate selected one or more wakefulness inducers 300. Wakefulness induction control device 100 may further include storage 140 that stores, for each wakefulness inducer 300, the amount of decrease in the sleepiness level of user U with respect to the predetermined duration (i.e., the amount of change in the direction of increasing wakefulness of user U). In this case, controller 120 may actuate one or more wakefulness inducers 300 including wakefulness inducer 300 of which the amount of decrease in the sleepiness level of user U with respect to the predetermined duration stored in storage 140 is largest. To rephrase, controller 120 may actuate one or more wakefulness inducers 300 including wakefulness inducer 300 of which the amount of change in the sleepiness level of user U in the direction of increasing wakefulness of user U with respect to the predetermined duration stored in storage 140 is largest.

Sleepiness detector 110 and controller 120 are implemented, for example, with a central processing unit (CPU) and a control program stored in storage 140. Sleepiness detector 110 and controller 120 may each be implemented with a separate processor or may be implemented with a single processor.

Output 130 is an interface for outputting actuating information of wakefulness inducer 300 actuated by controller 120. Output 130 is connected, for example, to display 500, which is a display device such as a display, and outputs, to display 500, display information including characters and/or pictures, representing the actuating information of wakefulness inducer 300. Display 500 displays the acquired display information in the form of an image.

Examples of display 500 include a monitor device (display) constituted by a liquid crystal panel, an organic EL panel, or the like. In addition, a device having a display, such as a television set or an information terminal such as a smartphone and a tablet terminal, may be used as display 500.

Output 130 may be connected to a speaker or the like, for example, and output audio information indicating the content of control executed by controller 120.

The actuating information may include, for example, time information indicating the duration left until controller 120 stops wakefulness inducer 300. With this configuration, wakefulness induction control device 100, upon being connected to display 500 such as a display or a speaker, can present the duration that has passed after actuation of wakefulness inducer 300. This allows user U to easily recognize the duration that has passed after controller 120 has actuated wakefulness inducer 300 via display 500 such as a display or a speaker.

The actuating information may further include, for example, stop information that, when controller 120 has stopped wakefulness inducer 300, indicates that controller 120 has stopped wakefulness inducer 300. With this configuration, wakefulness induction control device 100 can reduce the possibility that user U mistakenly thinks that wakefulness inducer 300 has stopped due to a failure or the like.

Storage 140 is a storage device that stores a control program to be executed by sleepiness detector 110 and controller 120. Storage 140 may be, for example, a read only memory (ROM), a random access memory (RAM), a hard disk drive (HDD), a solid state drive (SSD), or the like.

Storage 140 may further store, for each wakefulness inducer 300, the amount of decrease in the sleepiness level of user U with respect to the predetermined duration. To rephrase, storage 140 may store the amount of change in the sleepiness level of user U in the direction of increasing wakefulness of user U with respect to the predetermined duration.

Wakefulness induction control device 100 may include a time tracker (not illustrated), such as a real time clock (RTC), for measuring the duration.

The present disclosure may be configured as a system that includes wakefulness induction control device 100 and one or more wakefulness inducers 300. To rephrase, wakefulness induction system 200 according to the present disclosure includes wakefulness induction control device 100 and wakefulness inducer(s) 300.

[Operation]

Now, an operation of wakefulness induction control device 100 and wakefulness induction system 200 according to an embodiment will be described with reference to FIGS. 4A to 15. In the following description, as the reference based on which the sleepiness level is determined, the relationship among the sleepiness level, the degree of sleepiness, and the characteristics examples illustrated in FIG. 3 is prestored in storage 140. In addition, in the following description, the reference value indicating that the sleepiness level is 3 is set.

Figure 4A:
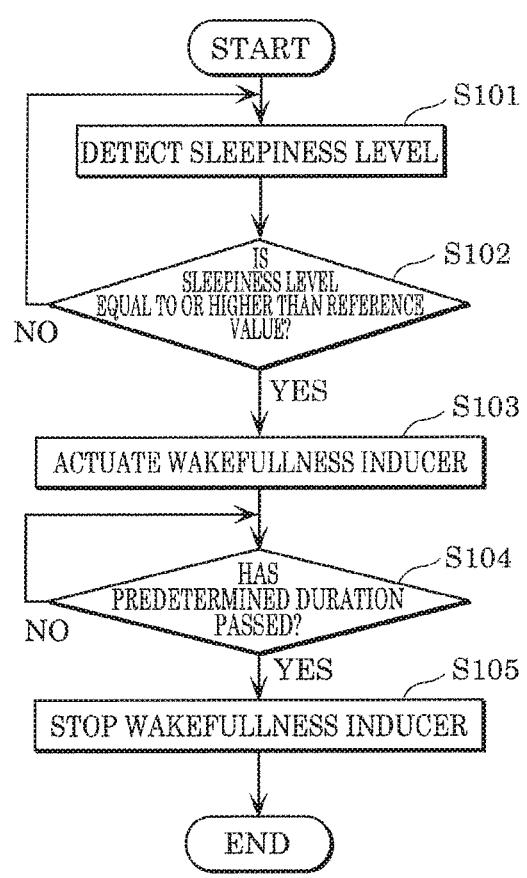
FIG. 4A is a flowchart illustrating a procedure through which a wakefulness induction control device according to an embodiment stops a wakefulness inducer.

FIG. 4A is a flowchart illustrating a procedure through which wakefulness induction control device 100 according to the embodiment stops wakefulness inducer 300.

Sleepiness detector 110 detects the sleepiness level of user U (step S101). For example, sleepiness detector 110 detects the sleepiness level of user U by acquiring a moving image captured by imager 400 and analyzing the acquired moving image.

Then, controller 120 determines whether the sleepiness level detected by sleepiness detector 110 is equal to or higher than the reference value (step S102). When controller 120 has determined that the sleepiness level is neither equal to nor higher than the reference value (NO in step S102), sleepiness detector 110 and controller 120 continue to execute the operations in step S101 and step S102.

Meanwhile, when controller 120 has determined that the sleepiness level is equal to or higher than the reference value (YES in step S102), controller 120 actuates wakefulness inducer 300 (step S103).

Then, controller 120 determines whether the predetermined duration has passed (step S104). For example, wakefulness induction control device 100 may include the time tracker described above, and the time tracker may measure the duration for which wakefulness inducer 300 has been being actuated. Controller 120 may acquire the duration measured by the time tracker. When controller 120 has determined that the predetermined duration has not passed (NO in step S104), controller 120 continues to execute the operation in step S104.

Meanwhile, when controller 120 has determined that the predetermined duration has passed (YES in step S104), controller 120 stops wakefulness inducer 300 (step S105).

Figure 4B:
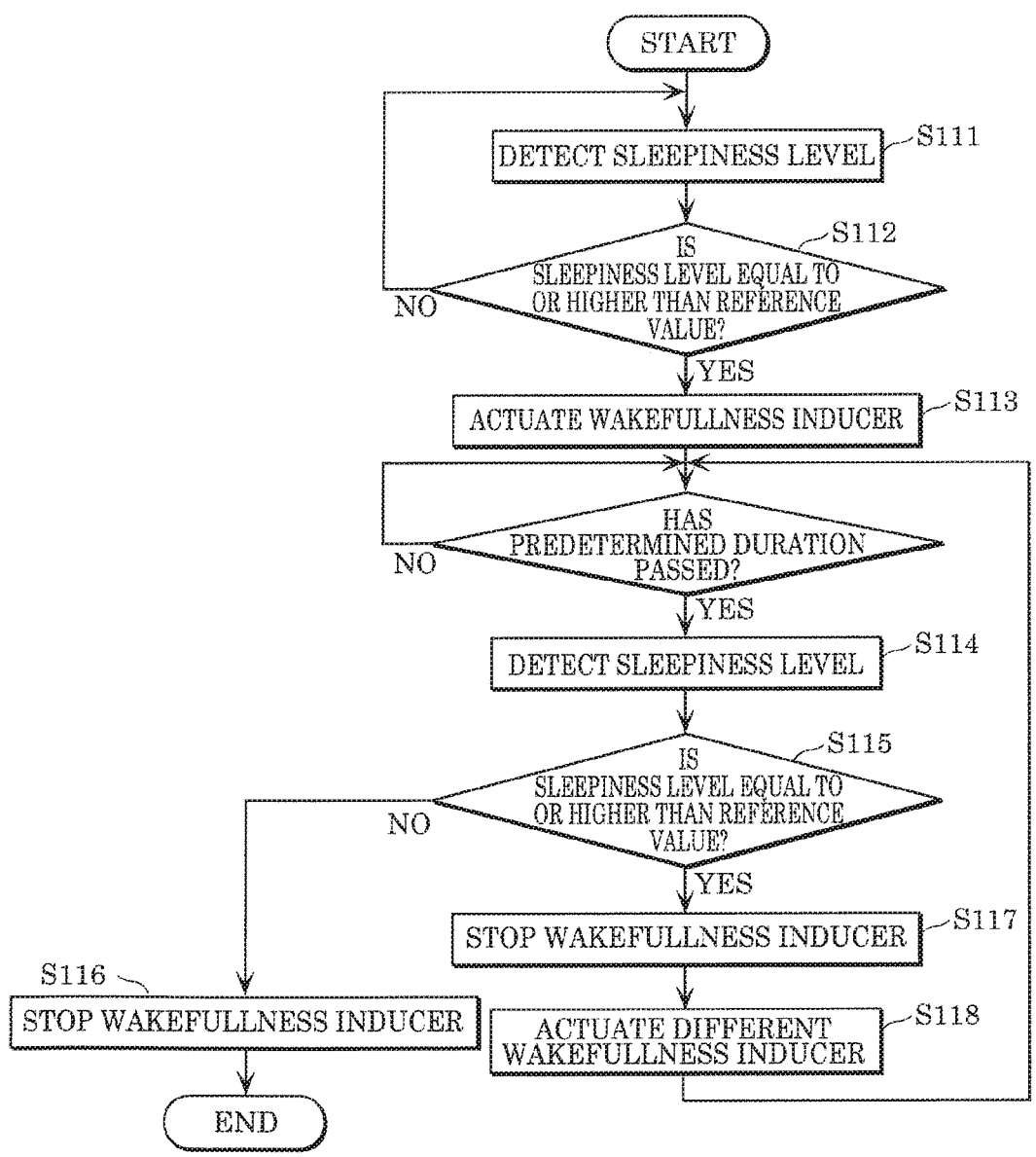
FIG. 4B is a flowchart illustrating another example of a procedure through which a wakefulness induction control device according to an embodiment stops a wakefulness inducer.

FIG. 4B is a flowchart illustrating another example of a procedure through which wakefulness induction control device 100 according to the embodiment stops wakefulness inducer 300.

Sleepiness detector 110 detects the sleepiness level of user U (step S111). For example, sleepiness detector 110 detects the sleepiness level of user U by acquiring a moving image captured by imager 400 and analyzing the acquired moving image.

Then, controller 120 determines whether the sleepiness level detected by sleepiness detector 110 is equal to or higher than the reference value (step S112). When controller 120 has determined that the sleepiness level is neither equal to nor higher than the reference value (NO in step S112), sleepiness detector 110 and controller 120 continue to execute the operations in step S111 and step S112.

Meanwhile, when controller 120 has determined that the sleepiness level is equal to or higher than the reference value (YES in step S112), controller 120 actuates wakefulness inducer 300 (step S113).

Then, after the predetermined duration has passed, sleepiness detector 110 detects the sleepiness level of user U (step S114).

Then, controller 120 determines whether the sleepiness level detected by sleepiness detector 110 is equal to or higher than the reference value (step S115). When controller 120 has determined that the sleepiness level is neither equal to nor higher than the reference value (NO in step S115), controller 120 stops wakefulness inducer 300 (step S116).

Meanwhile, when controller 120 has determined that the sleepiness level is equal to or higher than the reference value (YES in step S115), controller 120 stops wakefulness inducer 300 (step S117).

Then, controller 120 actuates wakefulness inducer 300 different from wakefulness inducer 300 that has been stopped, and after another predetermined duration has passed, controller 120 performs the operation in step S114.

In FIG. 4B, sleepiness detector 110 may detect the sleepiness level of user U in step S114. When the sleepiness level of user U has reached or fallen below the preset desired reference value before the predetermined duration passes, controller 120 stops wakefulness inducer 300. In this case, the wakefulness inducing method of wakefulness inducer 300 that has been being actuated conceivably has a high wakefulness inducing effect on user U. Therefore, when controller 120 actuates again wakefulness inducer 300 that has been actuated, controller 120 may reduce the set predetermined duration.

When the sleepiness level of user U fails to fall below the preset desired value before the predetermined duration passes, controller 120 stops currently actuated wakefulness inducer 300 and actuates different wakefulness inducer 300. With this configuration, wakefulness can be induced more effectively in the user.

Figure 4C:
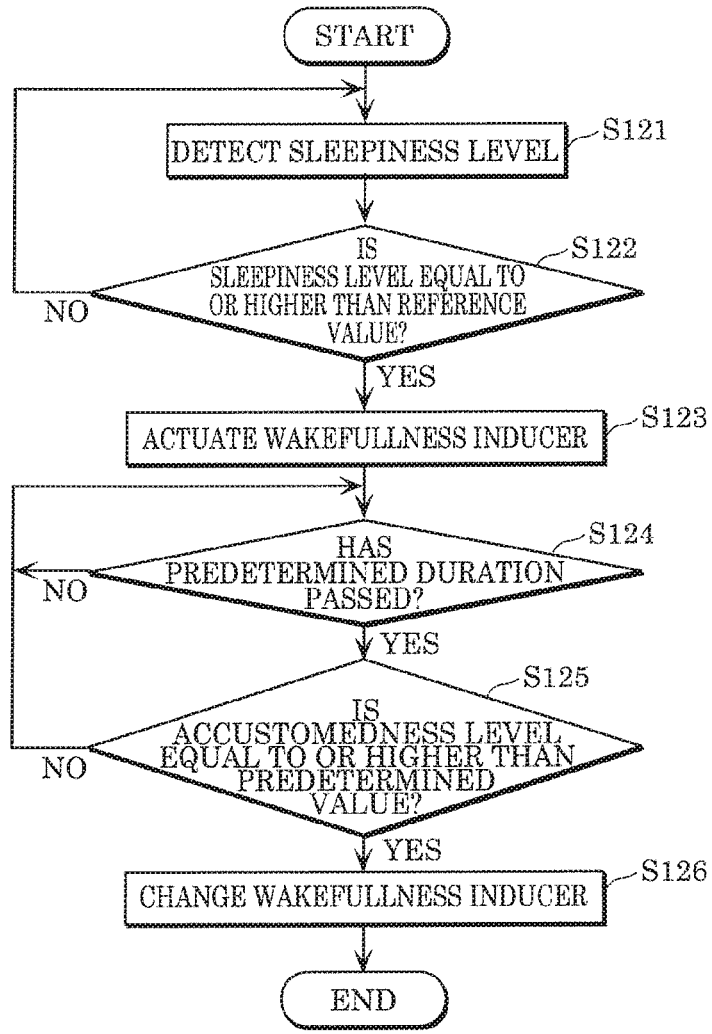
FIG. 4C is a flowchart illustrating another example of a procedure through which a wakefulness induction control device according to an embodiment stops a wakefulness inducer.

FIG. 4C is a flowchart illustrating another example of a procedure through which wakefulness induction control device 100 according to the embodiment stops wakefulness inducer 300.

Sleepiness detector 110 detects the sleepiness level of user U (step S121). For example, sleepiness detector 110 detects the sleepiness level of user U by acquiring a moving image captured by imager 400 and analyzing the acquired moving image.

Then, controller 120 determines whether the sleepiness level detected by sleepiness detector 110 is equal to or higher than the reference value (step S122). When controller 120 has determined that the sleepiness level is neither equal to nor higher than the reference value (NO in step S122), sleepiness detector 110 and controller 120 continue to execute the operations in step S121 and step S122.

Meanwhile, when controller 120 has determined that the sleepiness level is equal to or higher than the reference value (YES in step S122), controller 120 actuates wakefulness inducer 300 (step S123).

Then, controller 120 determines whether the predetermined duration has passed (step S124). For example, wakefulness induction control device 100 may include the time tracker described above, and the time tracker may measure the duration for which wakefulness inducer 300 has been being actuated. Controller 120 may acquire the duration measured by the time tracker. When controller 120 has determined that the predetermined duration has not passed (NO in step S124), controller 120 continues to execute the operation in step S124.

Meanwhile, when controller 120 has determined that the predetermined duration has passed (YES in step S124), controller 120 determines an accustomedness level indicating the level of accustomedness of user U to wakefulness inducer 300 (i.e., the degree of accustomedness) (step S125). Specifically, in step S125, controller 120 determines whether the accustomedness level of user U is equal to or higher than a predetermined value. For example, a higher accustomedness level indicates that the user has become more accustomed to the wakefulness inducing method of the currently actuated wakefulness inducer.

The accustomedness level of user U may be determined, for example, based on the sleepiness level of user U detected by sleepiness detector 110. To be more specific, the accustomedness level of user U to the wakefulness inducing method may be determined based on a difference of a change in the sleepiness level of user U detected by sleepiness detector 110 between when a predetermined wakefulness inducer (e.g., wakefulness inducer 300a) has been actuated in a previous instance and when the same wakefulness inducer (e.g., wakefulness inducer 300a) is actuated in a current instance. The accustomedness level of user U may be determined by controller 120, for example, based on a desired preset condition, such as the accustomedness level of 1, 2, 3, 4, 5, or the like, and based on the difference of the change in the sleepiness level. In addition, the predetermined value of the accustomedness level may be set as desired and may be prestored in storage 140, for example.

The accustomedness level of user U may be determined through a technique other than the one described above, and as long as controller 120 controls wakefulness inducer 300 in consideration of the current condition of user U, there is no limitation on the technique for determining the accustomedness level of user U.

When controller 120 has determined, based on the result of the accustomedness level determination, that user U has not become accustomed to wakefulness inducer 300, controller 120 determines whether another predetermined duration has passed since that point (step S124).

Meanwhile, when controller 120 has determined, based on the result of the accustomedness level determination, that user U has become accustomed, the effect of wakefulness inducer 300 has worn off, and thus controller 120 changes the method of actuating wakefulness inducer 300 (step S126). For example, controller 120 compares the accustomedness level of user U calculated based on the change over time in the sleepiness level of user U detected by sleepiness detector 110 against the predetermined value of the accustomedness level stored in storage 140 (step S125). When controller 120 has determined that the accustomedness level of user U is equal to or higher than the predetermined value (YES in step S125), controller 120 changes the method of actuating wakefulness inducer 300 (step S126).

In this manner, controller 120 may, for example, determine the accustomedness level indicating the level of accustomedness of user U to wakefulness inducer 300 based on the sleepiness level of user U detected by sleepiness detector 110 and change the method of actuating wakefulness inducer 300 based on the determined accustomedness level of user U.

With this configuration, when controller 120 has determined that user U has become accustomed to the wakefulness inducing method of wakefulness inducer 300, controller 120 changes the wakefulness inducing method. Accordingly, a decrease in the wakefulness inducing effect on user U is further suppressed.

Here, a lower accustomedness level may indicate that the user has become more accustomed to the wakefulness inducing method of the currently actuated wakefulness inducer. In this case, in step S125, controller 120 may determine whether the accustomedness level of user U is less than the predetermined value and control wakefulness inducer 300 based on the determined accustomedness level.

Figure 5A:
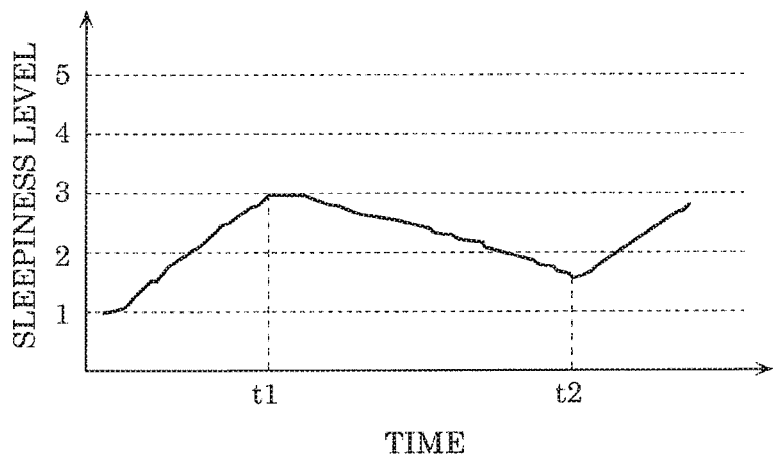
FIG. 5A illustrates an example of a change in the sleepiness level with respect to the time obtained when a wakefulness induction control device according to an embodiment is used.

FIG. 5A illustrates an example of a change in the sleepiness level with respect to the time obtained when wakefulness induction control device 100 according to the embodiment is used. FIG. 5A is a graph illustrating an example of a change in the sleepiness level of user U obtained when wakefulness induction system 200 is operated in accordance with the flowchart illustrated in FIG. 4A. In the graph illustrated in FIG. 5A, the horizontal axis represents the time, and the vertical axis represents the sleepiness level of user U.

As illustrated in FIG. 5A, the sleepiness level of user U rises along with the passage of time. At time t1, the sleepiness level of user U reaches 3. At this point, controller 120 actuates wakefulness inducer 300. As more time passes, the sleepiness level of user U gradually decreases. At time t2, controller 120 stops wakefulness inducer 300. In other words, in FIG. 5A, the predetermined duration corresponds to the duration from time t1 to time t2. In this manner, wakefulness induction control device 100 stops wakefulness inducer 300 when the predetermined duration has passed regardless of the effect of wakefulness inducer 300 on inducing wakefulness in user U.

Figure 5B:
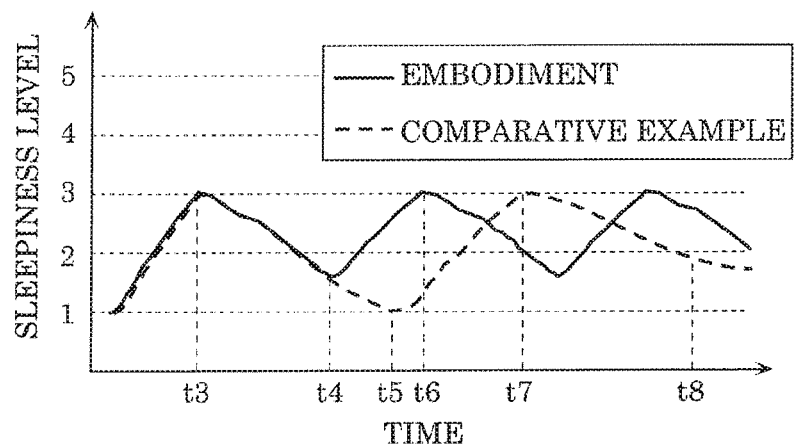
FIG. 5B illustrates an example of a change in the sleepiness level with respect to the time obtained when a wakefulness induction control device according to a comparative example is used.

FIG. 5B illustrates an example of a change in the sleepiness level with respect to the time obtained when a wakefulness induction control device according to a comparative example is used. The solid line illustrated in FIG. 5B indicates an example of a change in the sleepiness level with respect to the time obtained when wakefulness induction control device 100 according to the embodiment is used, and the dashed line illustrated in FIG. 5B indicates an example of a change in the sleepiness level with respect to the time obtained when wakefulness induction control device 100 according to the comparative example is used.

In the following description, the wakefulness induction control device according to the comparative example illustrated in FIG. 5B performs control of actuating a wakefulness inducer when the sleepiness level of the user is 3 and then stopping the wakefulness inducer when the sleepiness level of the user has become 1. In addition, FIG. 5B illustrates an example of a change in the sleepiness level obtained when the same wakefulness inducer is actuated in the wakefulness induction control device according to the comparative example and in the wakefulness induction control device according to the embodiment.

As illustrated in FIG. 5B, the sleepiness level of user U rises along with the passage of time. At time t3, the sleepiness level of user U reaches 3.

At this point, the wakefulness induction control device according to the embodiment and the wakefulness induction control device according to the comparative example each actuate the wakefulness inducer. As more time passes, the sleepiness level of user U gradually decreases.

At time t4, the wakefulness induction control device according to the embodiment stops the wakefulness inducer. In other words, in FIG. 5B, the predetermined duration corresponds to the duration from time t3 to time t4. In this manner, the wakefulness induction control device according to the embodiment stops the wakefulness inducer when the predetermined duration has passed regardless of the effect of the wakefulness inducer on inducing wakefulness in user U. In addition, at time t6, the wakefulness induction control device according to the embodiment actuates the wakefulness inducer again since the sleepiness level of user U has reached 3. In this manner, the wakefulness induction control device according to the embodiment intermittently (repeatedly) actuates the wakefulness inducer by stopping the wakefulness inducer after the predetermined duration and actuating the wakefulness inducer again when the sleepiness level of the user has met the predetermined reference. Thus, user U is less likely to become accustomed to the wakefulness inducing method executed by the wakefulness inducer, and even if the wakefulness inducer is used repeatedly, a situation where the sleepiness level decreases less easily with respect to the time is suppressed.

Meanwhile, at time t4, the wakefulness induction control device according to the comparative example does not stop the wakefulness inducer since the sleepiness level of user U has not reached 1. At time t5, the wakefulness induction control device according to the comparative example determines that the sleepiness level of user U has reached 1 and stops the wakefulness inducer. In addition, at time t7, the wakefulness induction control device according to the comparative example actuates the wakefulness inducer again since the sleepiness level of user U has reached 3.

Here, with the wakefulness induction control device according to the comparative example, the amount of decrease in the sleepiness level with respect to the time after time t7 is smaller than the amount of decrease in the sleepiness level of user U with respect to the time within the duration from time t3 to time t5. In other words, as compared to the wakefulness induction control device according to the embodiment, with the wakefulness induction control device according to the comparative example, user U is more accustomed to the wakefulness inducing method executed by the wakefulness inducer, and the sleepiness level with respect to the time is less likely to decrease when the wakefulness inducer is used repeatedly. Furthermore, with the wakefulness induction control device according to the comparative example, the sleepiness level is even less likely to decrease with respect to the time at time t8. In such a case, there is a possibility that, even through the effect of inducing wakefulness in user U is not observed, the wakefulness inducer is actuated for an extended period of time since the sleepiness level of user U does not decrease.

As described above, wakefulness induction control device 100 includes sleepiness detector 110 that detects the sleepiness level indicating the degree of sleepiness of user U, and controller 120. Controller 120 actuates wakefulness inducer 300 that induces wakefulness in user U when the sleepiness level detected by sleepiness detector 110 meets the predetermined reference and stops wakefulness inducer 300 when the predetermined duration has passed after actuation of wakefulness inducer 300.

Thus, controller 120 automatically stops wakefulness inducer 300 when the predetermined duration has passed. Therefore, even when user U has used wakefulness induction control device 100 repeatedly, user U is kept from becoming accustomed to the method of inducing wakefulness. In other words, wakefulness induction control device 100 according to the present disclosure can suppress a decrease in the wakefulness inducing effect by making user U less likely to become accustomed to the wakefulness inducing method. In addition, as wakefulness inducer 300 is operated intermittently, the amount of energy consumption, such as electric power, can be reduced, as compared to the case in which wakefulness inducer 300 continues to be operated for an extended period of time.

As described above, the present disclosure may be configured as wakefulness induction system 200 that includes wakefulness induction control device 100 and one or more wakefulness inducers 300.

With wakefulness induction system 200 configured as described above, user U is less likely to become accustomed to the method of inducing wakefulness in user U implemented by wakefulness inducer 300. In other words, wakefulness induction system 200 can suppress a decrease in the wakefulness inducing effect by making user U less likely to become accustomed to the wakefulness inducing method.

Figure 6A:
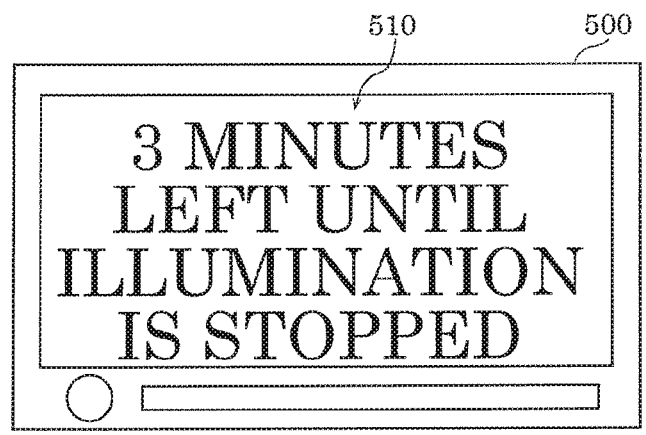
FIG. 6A illustrates an example of an output result for notifying a user of the duration left until a wakefulness induction control device according to an embodiment stops actuating a wakefulness inducer.

FIG. 6A illustrates an example of an output result for notifying the user of the duration left until wakefulness induction control device 100 according to the embodiment stops wakefulness inducer 300.

When the predetermined duration has passed, wakefulness induction control device 100 automatically stops wakefulness inducer 300. Therefore, it is difficult for user U to determine whether wakefulness inducer 300 has been stopped by wakefulness induction control device 100 or wakefulness inducer 300 has stopped unexpectedly due to a failure or the like.

For example, an illumination device that emits illumination light may be used as wakefulness inducer 300. In this case, in step S104 illustrated in FIG. 4A, output 130 may output information that causes image 510 illustrated in FIG. 6A to be displayed in display 500, for example. This configuration makes it easier for user U to determine whether wakefulness inducer 300 has been stopped by controller 120 or wakefulness inducer 300 has stopped unexpectedly due to a failure or the like.

The information output by output 130 is not limited to image information to be displayed in display 500. For example, when wakefulness induction system 200 includes a speaker, controller 120 may cause output 130 to output audio information. For example, when controller 120 stops wakefulness inducer 300, controller 120 may cause output 130 to output audio information indicating that wakefulness inducer 300 is to be stopped. With this configuration, wakefulness induction control device 100 may notify user U that wakefulness inducer 300 is to be stopped.

Figure 6B:
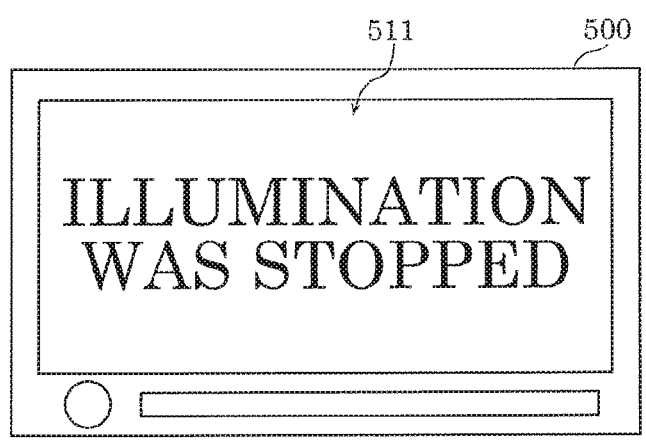
FIG. 6B illustrates an example of an output result for notifying a user that a wakefulness induction control device according to an embodiment has stopped actuating a wakefulness inducer.

FIG. 6B illustrates an example of an output result for notifying the user that wakefulness induction control device 100 according to the embodiment has stopped wakefulness inducer 300.

In step S105 illustrated in FIG. 4A, output 130 may output information that causes image 511 illustrated in FIG. 6B to be displayed in display 500, for example.

Now, a procedure through which controller 120 determines the predetermined duration will be described.

Figure 7:
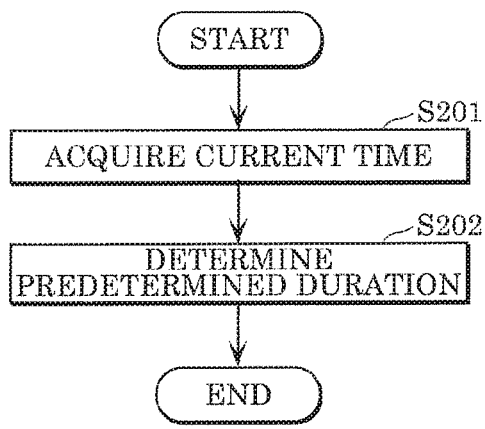
FIG. 7 is a flowchart illustrating an example of a procedure through which a wakefulness induction control device according to an embodiment determines a predetermined duration.

FIG. 7 is a flowchart illustrating an example of a procedure through which wakefulness induction control device 100 according to the embodiment determines the predetermined duration.

Controller 120 acquires a current time (step S201). There is no particular limitation on the method of acquiring the current time. For example, when wakefulness induction control device 100 includes a time tracker, such as an RTC, controller 120 may acquire the current time from the RTC.

Then, controller 120 determines the predetermined duration based on the acquired current time (step S202). For example, the predetermined duration may be preset as desired, and controller 120 may determine a new predetermined duration by changing the preset predetermined duration in accordance with the current time.

For example, the predetermined duration may be preset to 10 minutes. In this case, when the current time is 10:00 a.m., controller 120 may determine the predetermined duration to be eight minutes, which is two minutes shorter than the preset predetermined duration. In addition, when the current time is 15:00 in the afternoon, controller 120 may determine the predetermined duration to be 12 minutes, which is two minutes longer than the preset predetermined duration. In this case, controller 120 may determine the predetermined duration depending on whether it is a time period when the user is likely to feel sleepy.

As described above, controller 120 may change the predetermined duration in accordance with the current time. With this configuration, the actuating duration of wakefulness inducer 300 is adjusted in accordance with the time that is estimated to be when user U is likely to feel sleepy. Accordingly, this configuration can increase the wakefulness inducing effect on user U.

Figure 8:
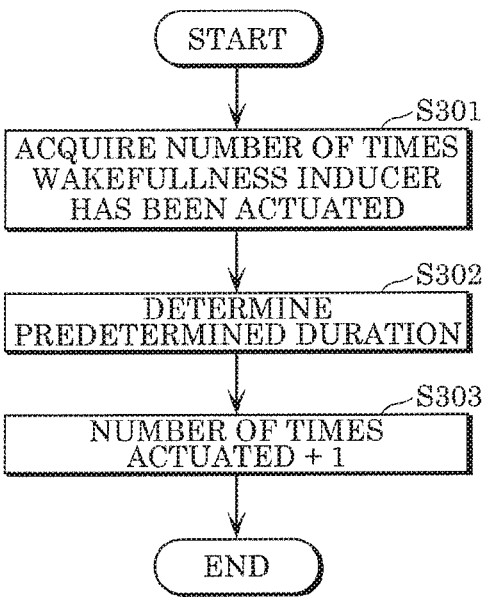
FIG. 8 is a flowchart illustrating another example of a procedure through which a wakefulness induction control device according to an embodiment determines a predetermined duration.

FIG. 8 is a flowchart illustrating another example of a procedure through which wakefulness induction control device 100 according to the embodiment determines the predetermined duration.

As illustrated in FIG. 8, controller 120 acquires the number of times wakefulness inducer 300 has been actuated (step S301).

Then, controller 120 determines the predetermined duration based on the acquired number of times wakefulness inducer 300 has been actuated (step S302). For example, the predetermined duration may be preset as desired, and controller 120 may determine a new predetermined duration by changing the preset predetermined duration in accordance with the number of times wakefulness inducer 300 has been actuated.

For example, the predetermined duration may be preset to 10 minutes. In this case, when the number of times wakefulness inducer 300 has been actuated is no less than 10, controller 120 may determine the predetermined duration to be eight minutes, which is two minutes shorter than the preset predetermined duration. In addition, when the number of times wakefulness inducer 300 has been actuated is lower than 10, controller 120 may determine the predetermined duration to be 12 minutes, which is two minutes longer than the preset predetermined duration. When wakefulness is induced in user U repeatedly by wakefulness inducer 300, the possibility that user U becomes accustomed to the wakefulness inducing method increases. Therefore, changing the predetermined duration in accordance with the number of times wakefulness inducer 300 has been actuated makes it possible to suppress a decrease in the wakefulness inducing effect on user U.

Next, controller 120 increments the number of times wakefulness inducer 300 has been actuated by one and stores the new number of times wakefulness inducer 300 has been actuated into storage 140 (step S303).

The time period for which the number of times wakefulness inducer 300 has been actuated is integrated may be, for example, one day or one week and may be set as desired.

In this manner, controller 120 may change the predetermined duration in accordance with the number of times wakefulness inducer 300 has been actuated. With this configuration, user U is less likely to become accustomed to the wakefulness inducing method of wakefulness inducer 300. Accordingly, this configuration suppresses a decrease in the wakefulness inducing effect on user U.

Figure 9A:
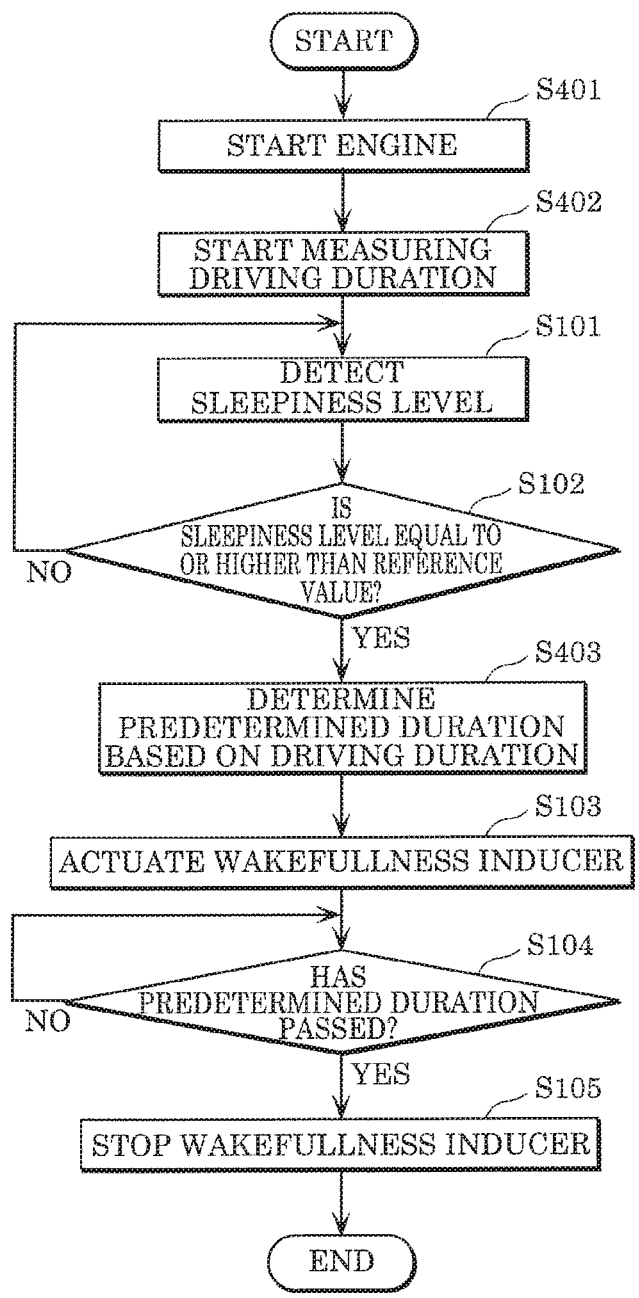
FIG. 9A is a flowchart illustrating an example of a procedure for determining a predetermined duration in a case in which a wakefulness induction control device according to an embodiment is disposed in a vehicle.

FIG. 9A is a flowchart illustrating an example of a procedure for determining the predetermined duration in a case in which wakefulness induction control device 100 according to the embodiment is disposed in vehicle 600.

User U may start an engine of vehicle 600 (step S401).

Then, controller 120 starts measuring the driving duration, which is the duration for which the engine of vehicle 600 is running (step S402). There is no particular limitation on the method through which controller 120 recognizes that the engine of vehicle 600 has been started. For example, wakefulness induction control device 100 may include an acquirer (not illustrated), which is an interface to be connected to a user interface, such as a touch panel, for acquiring an instruction from user U. In this case, controller 120 may start measuring the driving duration when the acquirer has acquired, from user U, an instruction indicating that user U has started the engine of vehicle 600. In addition, for example, when vehicle 600 includes an engine control unit (ECU), wakefulness induction control device 100 may include a communicator (not illustrated), which is an interface to be connected to the ECU. In this case, controller 120 may start measuring the driving duration when the communicator has acquired, from the ECU, a signal indicating that user U has started the engine of vehicle 600.

Then, sleepiness detector 110 and controller 120 execute operations similar to those in step S101 and step S102 illustrated in FIG. 4A.

When controller 120 has determined that the sleepiness level is equal to or higher than the reference value (YES in step S102), controller 120 determines the predetermined duration based on the measured driving duration (step S403), For example, the predetermined duration may be preset as desired, and controller 120 may determine a new predetermined duration by changing the preset predetermined duration in accordance with the driving duration.

For example, the predetermined duration may be preset to 10 minutes. In this case, when the driving duration is less than one hour, controller 120 may determine the predetermined duration to be 12 minutes, which is two minutes longer than the preset predetermined duration. In addition, when driving duration is no less than one hour, controller 120 may determine the predetermined duration to be eight minutes, which is two minutes shorter than the preset predetermined duration. In this manner, controller 120 may determine the predetermined duration in accordance with whether user U is in a state in which user U has become accustomed to the wakefulness inducing method.

Then, controller 120 executes operations similar to those in step S103 to step S105 illustrated in FIG. 4A.

The driving duration may be remeasured when the engine of vehicle 600 has been stopped, for example, or the driving duration may be the total driving duration, which is the integrated duration of the day's driving duration.

Figure 9B:
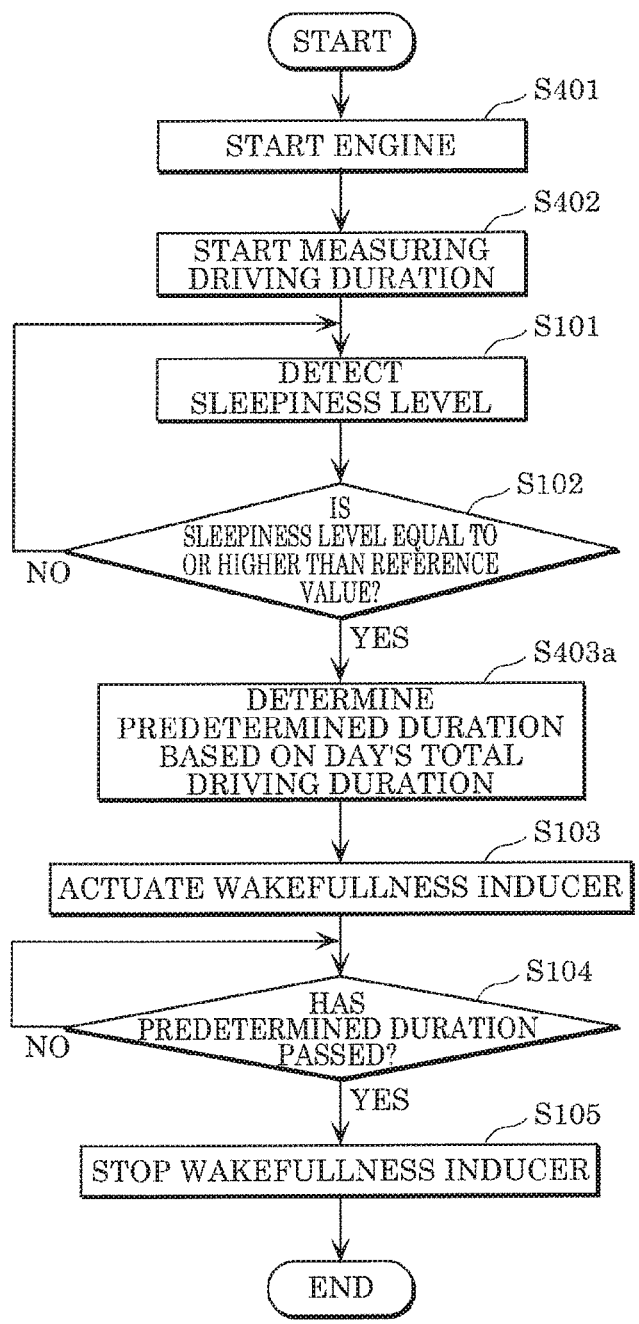
FIG. 9B is a flowchart illustrating another example of a procedure for determining a predetermined duration in a case in which a wakefulness induction control device according to an embodiment is disposed in a vehicle.

FIG. 9B is a flowchart illustrating another example of a procedure for determining the predetermined duration in a case in which wakefulness induction control device 100 according to the embodiment is disposed in vehicle 600.

As illustrated in FIG. 9B, this flowchart differs from the flowchart illustrated in FIG. 9A in terms of the method of determining the predetermined duration in step S403a.

In step S403a, controller 120 determines the predetermined duration based on the day's total driving duration. For example, the predetermined duration may be preset as desired, and controller 120 may determine a new predetermined duration by changing the preset predetermined duration in accordance with the day's total driving duration.

For example, the predetermined duration may be preset to 10 minutes. In this case, when the driving duration is less than one hour, controller 120 may determine the predetermined duration to be 12 minutes, which is two minutes longer than the preset predetermined duration. In addition, in this case, when the driving duration is no less than one hour, controller 120 may determine the predetermined duration to be eight minutes, which is two minutes shorter than the preset predetermined duration. In other words, controller 120 may change the predetermined duration to make the predetermined duration shorter as the driving duration increases. In this manner, controller 120 may determine the predetermined duration in accordance with whether the user is in a state in which user U has become accustomed to the wakefulness inducing method. Controller 120 may change the predetermined duration to make the predetermined duration longer as the driving duration increases.

In step S105 illustrated in FIGS. 9A and 9B, controller 120 may perform control of stopping wakefulness inducer 300 and cause output 130 to output information that causes display 500, a speaker (not illustrated), or the like to operate. For example, controller 120 performs control of stopping wakefulness inducer 300 and causes output 130 to output image information, audio information, or the like for prompting user U to take a rest. This configuration makes it easier for user U to realize that user U is in an environment that makes user U himself/herself sleepy.

When wakefulness induction system 200 includes a plurality of wakefulness inducers 300 that differ in the wakefulness inducing method, controller 120 may select one or more wakefulness inducers 300 to be actuated from the plurality of wakefulness inducers 300 in accordance with an attribute of user U serving as the driver and actuate selected wakefulness inducer(s) 300.

For example, the attribute of user U is information such as the age, the gender, or the physique of user U. There is no particular limitation on the method through which controller 120 estimates the attribute of user U. For example, controller 120 may estimate the attribute of user U based on an image captured by imager 400.

In addition, for example, wakefulness induction control device 100 may include an interface (not illustrated) for acquiring the attribute of user U. In this case, for example, user U connects an information terminal, such as a smartphone, owned by user U to the stated interface. User U transmits the attribute of user U to wakefulness induction control device 100 by operating the information terminal. Controller 120 may acquire the attribute of user U from the information terminal via the interface. In this case, user U may input, as the attribute, information such as the temperature, the music, or the scent that user U desires.

The attribute of user U may include information for identifying individual user U. Specifically, controller 120 may acquire information for identifying user U from an information terminal, such as a smartphone, owned by user U. For example, controller 120 may identify user U by acquiring information for identifying user U serving as the driver from the information terminal and select wakefulness inducer 300 to be actuated in accordance with identified user U.

In this manner, controller 120 may select wakefulness inducer 300 to be actuated based on the estimated and/or acquired attribute of user U.

With this configuration, controller 120 can actuate wakefulness inducer 300 that is estimated to have a high wakefulness inducing effect on user U. Therefore, wakefulness induction control device 100 can effectively induce wakefulness in the user.

The interface may be an interface for connecting to the information terminal via a cable or may be a communication interface for connecting to the information terminal wirelessly.

Thus, as illustrated in FIGS. 9A and 9B, when wakefulness induction control device 100 is installed in vehicle 600, controller 120 may determine the predetermined duration in accordance with the driving duration of user U. In this case, controller 120 may determine the predetermined duration in accordance with the day's total driving duration of user U. This configuration can make user U even less likely to become accustomed to the wakefulness inducing method of wakefulness inducer 300. Accordingly, this configuration further suppresses a decrease in the wakefulness inducing effect on user U. In this manner, controller 120 may determine the predetermined duration from when wakefulness inducer 300 starts being actuated to when wakefulness inducer 300 is stopped in accordance with the scene in which wakefulness induction system 200 is used.

As described above, wakefulness induction control device 100 may be connected to a plurality of wakefulness inducers 300 that differ in the wakefulness inducing method of inducting wakefulness in user U. To rephrase, wakefulness induction system 200 may include a plurality of wakefulness inducers 300 that differ in the wakefulness inducing method of inducing wakefulness in user U.

In the case described below, wakefulness induction system 200 includes a plurality of wakefulness inducers 300 that differ in the wakefulness inducing method of inducing wakefulness in user U. In the following description, wakefulness induction system 200 includes first wakefulness inducer 300a serving as an example of wakefulness inducer 300 and second wakefulness inducer 300b that differs from first wakefulness inducer 300a in the wakefulness inducing method.

Figure 10:
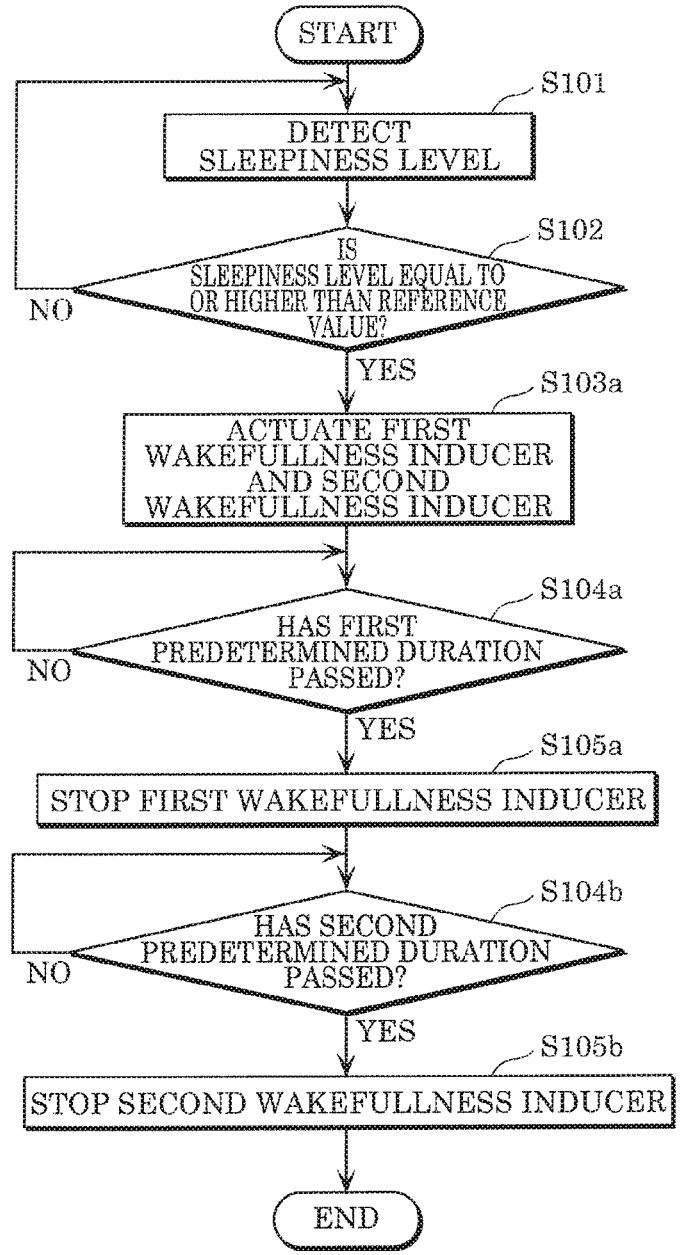
FIG. 10 is a flowchart illustrating a procedure for stopping each wakefulness inducer when a wakefulness induction control device according to an embodiment actuates a plurality of wakefulness inducers.

FIG. 10 is a flowchart illustrating a procedure for stopping each wakefulness inducer 300 when wakefulness induction control device 100 according to the embodiment actuates a plurality of wakefulness inducers 300. A first predetermined duration described below is shorter than a second predetermined duration.

First, sleepiness detector 110 and controller 120 execute operations similar to those in step S101 and step S102 illustrated in FIG. 4A.

Then, when controller 120 has determined that the sleepiness level is equal to or higher than the reference value (YES in step S102), controller 120 actuates first wakefulness inducer 300a and second wakefulness inducer 300b (step S103a).

For example, following step S103a, controller 120 determines whether the first predetermined duration has passed for first wakefulness inducer 300a (step S104a). When controller 120 has determined that the first predetermined duration has not passed (NO in step S104a), controller 120 continues to execute the operation in step S104a. Meanwhile, when controller 120 has determined that the first predetermined duration has passed (YES in step S104a), controller 120 stops wakefulness inducer 300a (step S105a).

In addition, controller 120 determines whether the second predetermined duration has passed (step S104b). When controller 120 has determined that the second predetermined duration has not passed (NO in step S104b), controller 120 continues to execute the operation in step S104b. Meanwhile, when controller 120 has determined that the second predetermined duration has passed (YES in step S104b), controller 120 stops wakefulness inducer 300b (step S105b).

In this manner, when wakefulness induction control device 100 is connected to the plurality of wakefulness inducers 300, wakefulness inducers 300 may be stopped at the predetermined durations (the first predetermined duration and the second predetermined duration described above) corresponding to respective wakefulness inducers 300. Specifically, controller 120 may stop each of the plurality of wakefulness inducers 300, one by one, when the predetermined duration set differently for each of the plurality of wakefulness inducers 300 has passed after actuation of the plurality of wakefulness inducers 300. With this configuration, wakefulness induction control device 100 can make user U even less likely to become accustomed in accordance with the wakefulness inducing method. Accordingly, this configuration further suppresses a decrease in the wakefulness inducing effect on user U.

Controller 120 may actuate each wakefulness inducer 300 simultaneously or may actuate each wakefulness inducer at a timing corresponding to each wakefulness inducer 300.

Controller 120 may randomly select wakefulness inducer 300 to be actuated. To rephrase, controller 120 may randomly select one or more wakefulness inducers 300 from the plurality of wakefulness inducers 300 and actuate selected one or more wakefulness inducers 300.

This configuration makes it easier to keep same wakefulness inducer 300 of the plurality of wakefulness inducers 300 from being actuated continuously. Therefore, user U is less likely to become accustomed to the wakefulness inducing method of each wakefulness inducer 300. In other words, this configuration further suppresses a decrease in the wakefulness inducing effect on user U.

Figure 11:
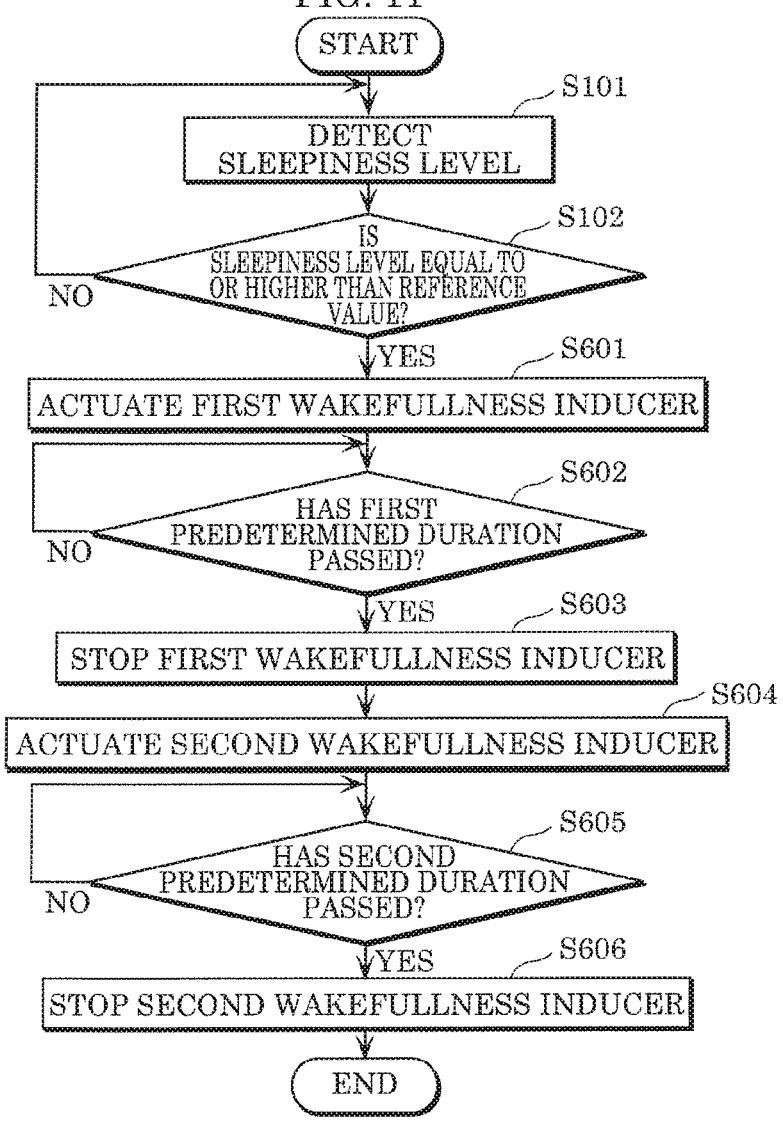
FIG. 11 is a flowchart illustrating a procedure through which a wakefulness induction control device according to an embodiment actuates a plurality of wakefulness inducers at different timings.

FIG. 11 is a flowchart illustrating a procedure through which wakefulness induction control device 100 according to the embodiment actuates a plurality of wakefulness inducers 300 at different timings.

First, sleepiness detector 110 and controller 120 execute operations similar to those in step S101 and step S102 illustrated in FIG. 4A.

Then, when controller 120 has determined that the sleepiness level is equal to or higher than the reference value (YES in step S102), controller 120 actuates first wakefulness inducer 300a (step S601).

Next, controller 120 determines whether the first predetermined duration has passed (step S602). When controller 120 has determined that the first predetermined duration has not passed (NO in step S602), controller 120 continues to execute the operation in step S602. Meanwhile, when controller 120 has determined that the first predetermined duration has passed (YES in step S602), controller 120 stops wakefulness inducer 300a (step S603).

Then, controller 120 actuates second wakefulness inducer 300b (step S604).

Next, controller 120 determines whether the second predetermined duration has passed (step S605). When controller 120 has determined that the second predetermined duration has not passed (NO in step S605), controller 120 continues to execute the operation in step S605. Meanwhile, when controller 120 has determined that the second predetermined duration has passed (YES in step S605), controller 120 stops wakefulness inducer 300b (step S606).

Controller 120 does not need to execute the operation in step S604 immediately following step S603. In other words, controller 120 may execute the operation in step S604 with an interval provided following step S603.

In this manner, controller 120 may successively actuate each wakefulness inducer 300 of the plurality of wakefulness inducers 300. Specifically, controller 120 may select one or more wakefulness inducers 300 of the plurality of wakefulness inducers 300 from the plurality of wakefulness inducers 300 and actuate selected one or more wakefulness inducers 300. Furthermore, controller 120 may stop each wakefulness inducer of one or more wakefulness inducers 300, one by one, when the predetermined duration set differently for each of the plurality of wakefulness inducers 300 has passed. Furthermore, controller 120 may actuate one or more wakefulness inducers 300 of wakefulness inducers 300 different from one or more wakefulness inducers 300 that have been stopped. This configuration can keep same wakefulness inducer 300 of the plurality of wakefulness inducers 300 from being actuated continuously. Thus, the plurality of wakefulness inducers 300 may be actuated with the number of times each wakefulness inducer 300 has been actuated kept from becoming uneven. Therefore, user U is even less likely to become accustomed to the wakefulness inducing method of each wakefulness inducer 300. In other words, this configuration further suppresses a decrease in the wakefulness inducing effect on user U.

Controller 120 may determine, following step S603, the sleepiness level of user U detected by sleepiness detector 110, and when the sleepiness level meets the predetermined reference, controller 120 may execute the operation in step S604.

Figure 12:
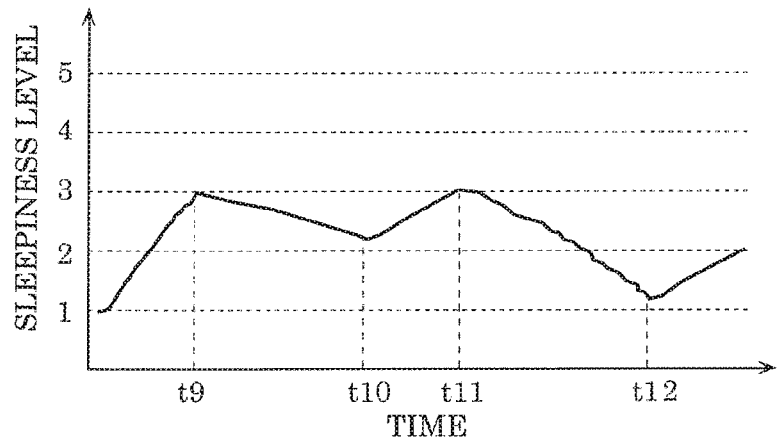
FIG. 12 illustrates another example of a change in the sleepiness level with respect to the time obtained when a wakefulness induction control device according to an embodiment is used.

FIG. 12 illustrates another example of a change in the sleepiness level with respect to the time obtained when wakefulness induction control device 100 according to the embodiment is used. FIG. 12 is a graph illustrating an example of a change in the sleepiness level of user U obtained when wakefulness induction system 200 is operated in accordance with the flowchart illustrated in FIG. 11. In the graph illustrated in FIG. 12, the horizontal axis represents the time, and the vertical axis represents the sleepiness level of user U.

As illustrated in FIG. 12, the sleepiness level of user U rises along with the passage of time. At time t9, the sleepiness level of user U reaches 3. At this point, controller 120 actuates wakefulness inducer 300a. As more time passes, the sleepiness level of user U gradually decreases. At time t10, controller 120 stops wakefulness inducer 300a. In other words, in FIG. 12, the first predetermined duration corresponds to the duration from time t9 to time t10.

Then, at time t11, controller 120 actuates wakefulness inducer 300b with a time interval spanning from time t10 to time t11 provided. As more time passes, the sleepiness level of user U gradually decreases. At time t12, controller 120 stops wakefulness inducer 300b. In other words, in FIG. 12, the second predetermined duration corresponds to the duration from time t11 to time t12.

FIG. 13 is a flowchart illustrating a first example of a procedure through which wakefulness induction control device 100 according to the embodiment selects wakefulness inducer 300 to be actuated.

First, sleepiness detector 110 and controller 120 execute operations similar to those in step S101 and step S102 illustrated in FIG. 4A.

Then, controller 120 acquires the current time (step S701). There is no particular limitation on the method through which controller 120 acquires the current time. For example, when wakefulness induction control device 100 includes a time tracker, such as an RTC, controller 120 may acquire the current time from the RTC.

Then, controller 120 selects wakefulness inducer 300 corresponding to the current time (step S702). There is no particular limitation on the reference based on which controller 120 selects wakefulness inducer 300 corresponding to the current time. For example, in the morning, controller 120 may preferentially select such wakefulness inducer 300 that emits a scent that stimulates the appetite of user U. In addition, for example, in the afternoon, controller 120 may preferentially select wakefulness inducer 300 that emits a sound, such as music. In addition, for example, at night, controller 120 may preferentially select wakefulness inducer 300 other than wakefulness inducer 300 that emits light.

Then, controller 120 actuates selected wakefulness inducer 300 (step S703).

In this manner, controller 120 may select one or more wakefulness inducers 300 from the plurality of wakefulness inducers 300 in accordance with the current time and actuate selected one or more wakefulness inducers 300. With this configuration, wakefulness inducer 300 is actuated in accordance with an environment in which user U is estimated to use wakefulness induction control device 100 in accordance with the current time. Accordingly, this configuration can increase the wakefulness inducing effect on user U.

FIG. 14 is a flowchart illustrating a second example of a procedure through which wakefulness induction control device 100 according to an embodiment selects wakefulness inducer 300 to be actuated.

First, sleepiness detector 110 and controller 120 execute operations similar to those in step S101 and step S102 illustrated in FIG. 4A.

Then, controller 120 acquires a current season (step S801). There is no particular limitation on the method through which controller 120 acquires the season. For example, for controller 120, for example, wakefulness induction control device 100 may include an acquirer (not illustrated), which is an interface to be connected to a user interface, such as a touch panel, for acquiring an instruction from user U. In this case, controller 120 may acquire information indicating the season from user U via the acquirer. In addition, for example, when wakefulness induction control device 100 includes a communication interface (not illustrated) connected to an external network, such as the internet, controller 120 may acquire information on the season from the external network via the communication interface.

Then, controller 120 selects wakefulness inducer 300 corresponding to the current season (step S802). There is no particular limitation on the reference based on which controller 120 selects wakefulness inducer 300 corresponding to the season.

For example, in summer and in winter, it is conceivably likely that the temperature of the interior is controlled with air conditioning equipment. Therefore, controller 120 may preferentially actuate wakefulness inducer 300 other the wakefulness inducer 300 that ventilates the interior to lower the $CO_2$ concentration with which the temperature is likely to be changed. Meanwhile, in spring and in fall, controller 120 may preferentially actuate wakefulness inducer 300 that ventilates the interior. With this configuration, wakefulness induction control device 100 can induce wakefulness in user U and can reduce the amount of energy use, such as electric power, of wakefulness inducer 300.

Then, controller 120 actuates selected wakefulness inducer 300 (step S803).

In this manner, controller 120 may select one or more wakefulness inducers 300 from the plurality of wakefulness inducers 300 in accordance with the season and actuate selected one or more wakefulness inducers 300. With this configuration, wakefulness inducer 300 is actuated that is suitable for the season and that can induce wakefulness in user U with high energy efficiency. Accordingly, this configuration can increase the wakefulness inducing effect on user U.

Figure 15:
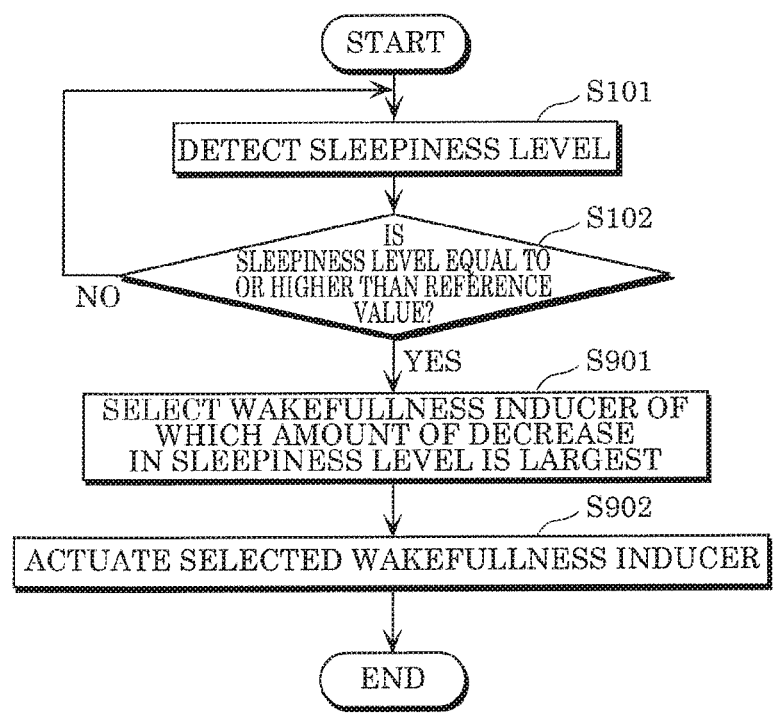
FIG. 15 is a flowchart illustrating a third example of a procedure through which a wakefulness induction control device according to an embodiment selects a wakefulness inducer to be actuated.

FIG. 15 is a flowchart illustrating a third example of a procedure through which wakefulness induction control device 100 according to the embodiment selects wakefulness inducer 300 to be actuated.

First, sleepiness detector 110 and controller 120 execute operations similar to those in step S101 and step S102 illustrated in FIG. 4A.

Then, controller 120 selects wakefulness inducer 300 of which an amount of decrease in the sleepiness level is largest (step S901).

Here, storage 140 stores, for each wakefulness inducer 300, the amount of decrease in the sleepiness level of user U with respect to the predetermined duration. For example, storage 140 stores, for each wakefulness inducer 300, the amount of decrease in the sleepiness level with respect to the duration from time t1 to time t2 indicated in FIG. 5A. Controller 120 selects wakefulness inducer 300 of which the amount of decrease in the sleepiness level of user U with respect to the predetermined duration stored in storage 140 is largest. To rephrase, controller 120 selects wakefulness inducer 300 of which the amount of change in the sleepiness level of user U with respect to the predetermined duration stored in storage 140 is largest in the direction of increasing wakefulness of user U.

Then, controller 120 actuates selected wakefulness inducer 300 (step S902).

In this manner, wakefulness induction control device 100 may include storage 140 that stores, for each wakefulness inducer 300, the amount of change in the sleepiness level of user U in the direction of increasing wakefulness of user U with respect to the predetermined duration. In other words, wakefulness induction control device 100 may include storage 140 that stores, for each wakefulness inducer 300, the amount of decrease in the sleepiness level of user U with respect to the predetermined duration. In this case, controller 120 may actuate one or more wakefulness inducers 300 including wakefulness inducer 300 of which the amount of change in the sleepiness level of user U with respect to the predetermined duration stored in storage 140 is largest. With this configuration, wakefulness can be induced effectively in user U in accordance with the characteristics of user U.

Controller 120 may update the amount of decrease in the sleepiness level of user U with respect to the predetermined duration stored, for each wakefulness inducer 300, in storage 140 each time wakefulness inducer 300 is used. With this configuration, controller 120 can actuate wakefulness inducer 300 that executes the wakefulness inducing method suitable for the current condition of user U.

Other Embodiments

Thus far, a wakefulness induction control device and a wakefulness induction system according to the present disclosure have been described based on embodiments and variations, but the present disclosure is not limited to the embodiments and the variations described above. For example, an embodiment obtained by making various modifications that a person skilled in the art can conceive of to the foregoing embodiments and variations and an embodiment achieved by combining, as desired, the constituent elements and the functions in the embodiments and the variations within the scope that does not depart from the spirit of the present disclosure are also encompassed by the present disclosure.

For example, wakefulness induction control device 100 and wakefulness induction system 200 are provided in vehicle 600 in the foregoing embodiments. However, the environment in which wakefulness induction control device 100 and wakefulness induction system 200 are used is not limited to a vehicle. For example, wakefulness induction control device 100 and wakefulness induction system 200 may be used inside a room, such as an office.

Figure 16:
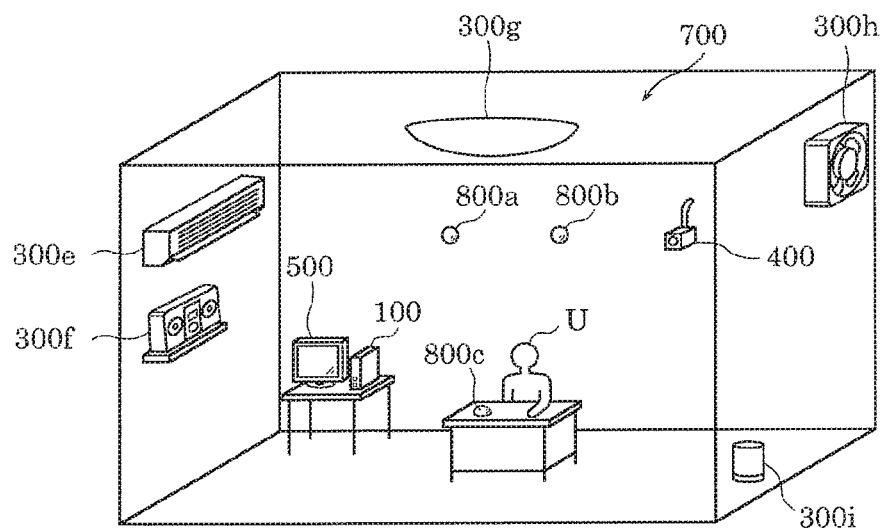
FIG. 16 is an illustration for describing another example of a system including a wakefulness induction control device according to an embodiment.

FIG. 16 is an illustration for describing another example of a system including wakefulness induction control device 100 according to an embodiment.

As illustrated in FIG. 16, wakefulness induction control device 100 is disposed in room interior 700. Wakefulness induction control device 100 is connected to a plurality of wakefulness inducers 300e to 300i that differ in the wakefulness inducing method via a wire (not illustrated) or the like. Wakefulness induction control device 100 is connected to one or more sensors 800a to 800c via a wire (not illustrated) or the like. In the following description, wakefulness inducers 300e to 300i are collectively referred to as wakefulness inducer(s) 300.

Sensors 800a to 800c are sensors that sense environment information indicating information on the environment, such as the temperature or the amount of light, in room interior 700 where user U is.

For example, wakefulness induction control device 100 may include an acquirer (not illustrated) that acquires the environment information of room interior 700 sensed by sensors 800a to 800c. In this case, controller 120 may control actuation of wakefulness inducer 300 based on the environment information sensed by sensors 800a to 800c.

In addition, for example, in addition to the reference value of the sleepiness level based on which controller 120 actuates wakefulness inducer 300, a stop reference value, which is a reference value of the sleepiness level based on which controller 120 stops wakefulness inducer 300, may also be set. When the sleepiness level of the user has reached the stop reference value before the predetermined duration passes after actuation of wakefulness inducer 300, controller 120 may stop wakefulness inducer 300.

When wakefulness induction system 200 includes a plurality of wakefulness inducers 300, controller 120 may, when the sleepiness level of user U fails to decrease even if one or more wakefulness inducers 300 have been actuated, actuate another one or more wakefulness inducers 300.

For example, the present disclosure can be implemented not only in the form of a wakefulness induction control device but also in the form of a program that includes, as steps, the processes performed by the constituent elements of the wakefulness induction control device or a recording medium, such as a computer readable digital versatile disc (DVD), having the program recorded therein. The program may be prerecorded in a recording medium or supplied to a recording medium via a broadband communication network including the internet.

In other words, the general or specific embodiments described above may be implemented in the form of a system, a device, an integrated circuit, a computer program, a computer readable recording medium, or any desired combination of a system, a device, an integrated circuit, a computer program, and a recording medium.

INDUSTRIAL APPLICABILITY

The present disclosure can be used in the form of a wakefulness induction control device and a wakefulness induction system that are less likely to make a user accustomed thereto and that can suppress a decrease in the wakefulness inducing effect. For example, the present disclosure is used in a device that is disposed in a vehicle, an office, or the like and that induces wakefulness in a person by actuating an air conditioner, an acoustic device, or the like.

The invention claimed is:

1. A wakefulness induction control device, comprising:
   a sleepiness detector that detects a sleepiness level indicating a degree of sleepiness of a person; and
   a controller that actuates a wakefulness inducer that induces wakefulness in the person when the sleepiness level detected by the sleepiness detector meets a predetermined reference,
   wherein the wakefulness induction control device is connected to a plurality of the wakefulness inducers that differ in a wakefulness inducing method of inducing wakefulness in the person, and
   wherein the controller selects one or more wakefulness inducers of the plurality of wakefulness inducers in accordance with an attribute of the person and actuates the one or more wakefulness inducers.

2. The wakefulness induction control device according to claim 1, wherein the controller stops the wakefulness inducer when a predetermined duration has passed after actuation of the wakefulness inducer and changes the predetermined duration in accordance with a current time.

3. The wakefulness induction control device according to claim 2, wherein the controller changes the predetermined duration in accordance with a number of times the wakefulness inducer has been actuated.

4. The wakefulness induction control device according to claim 2, wherein the controller changes the predetermined duration in accordance with a day's total driving duration of the person driving the vehicle.

5. The wakefulness induction control device according to claim 2, wherein
   the controller stops each of the plurality of wakefulness inducers when the predetermined duration set differently for each of the plurality of wakefulness inducers has passed after actuation of the plurality of wakefulness inducers.

6. The wakefulness induction control device according to claim 5, wherein the controller:
   actuates one or more wakefulness inducers of the plurality of wakefulness inducers,
   stops the one or more wakefulness inducers, one by one, when the predetermined duration set differently for each of the plurality of wakefulness inducers has passed, and
   further actuates one or more wakefulness inducers of the plurality of wakefulness inducers that are different from the one or more wakefulness inducers that have been stopped.

7. The wakefulness induction control device according to claim 5, wherein the controller selects one or more wakefulness inducers of the plurality of wakefulness inducers in accordance with a current time and actuates the one or more wakefulness inducers.

8. The wakefulness induction control device according to claim 5, wherein the controller selects one or more wakefulness inducers of the plurality of wakefulness inducers in accordance with a season and actuates the one or more wakefulness inducers.

9. The wakefulness induction control device according to claim 1, wherein the controller determines an accustomedness level indicating a level of accustomedness of the person to the wakefulness inducer and changes a method of actuating the wakefulness inducer based on the accustomedness level determined of the person.

10. A wakefulness induction system, comprising:
    the wakefulness induction control device according to claim 1; and
    the wakefulness inducer.

11. A wakefulness induction control device, comprising:
    a sleepiness detector that detects a sleepiness level indicating a degree of sleepiness of a person; and
    a controller that actuates a wakefulness inducer that induces wakefulness in the person when the sleepiness level detected by the sleepiness detector meets a predetermined reference, stops the wakefulness inducer when a predetermined duration has passed after actuation of the wakefulness inducer and changes the predetermined duration in accordance with a duration for which the person driving the a vehicle has continuously driven the vehicle.

12. The wakefulness induction control device according to claim 11, wherein the controller changes the predetermined duration in accordance with a day's total driving duration of the person driving the vehicle.

13. The wakefulness induction control device according to claim 11, wherein
    the wakefulness induction control device is connected to a plurality of the wakefulness inducers that differ in a wakefulness inducing method of inducing wakefulness in the person, and
    the controller stops each of the plurality of wakefulness inducers when the predetermined duration set differently for each of the plurality of wakefulness inducers has passed after actuation of the plurality of wakefulness inducers.

14. The wakefulness induction control device according to claim 13, wherein the controller selects one or more wakefulness inducers of the plurality of wakefulness inducers in accordance with a current time and actuates the one or more wakefulness inducers.

15. The wakefulness induction control device according to claim 13, wherein the controller selects one or more wakefulness inducers of the plurality of wakefulness inducers in accordance with a season and actuates the one or more wakefulness inducers.

16. The wakefulness induction control device according to claim 13, wherein the controller randomly selects one or more wakefulness inducers of the plurality of wakefulness inducers and actuates the one or more wakefulness inducers.

17. The wakefulness induction control device according to claim 13, wherein the controller selects one or more wakefulness inducers of the plurality of wakefulness inducers in accordance with an attribute of the person and actuates the one or more wakefulness inducers.

18. The wakefulness induction control device according to claim 13, further comprising:
    a storage that stores, for each of the plurality of wakefulness inducers, an amount of change in the sleepiness level of the person in a direction of increasing wakefulness of the person with respect to the predetermined duration, wherein the controller actuates one or more wakefulness inducers including a wakefulness inducer of which the amount of change stored in the storage is largest.

19. The wakefulness induction control device according to claim 11, wherein the controller determines an accustomedness level indicating a level of accustomedness of the person to the wakefulness inducer and changes a method of actuating the wakefulness inducer based on the accustomedness level determined of the person.

20. A wakefulness induction control device, comprising:
a sleepiness detector that detects a sleepiness level indicating a degree of sleepiness of a person and
a controller that actuates a wakefulness inducer that induces wakefulness in the person when the sleepiness level detected by the sleepiness detector meets a predetermined reference,
wherein the wakefulness induction control device is connected to a plurality of the wakefulness inducers that differ in a wakefulness inducing method of inducing wakefulness in the person, and
wherein the controller randomly selects one or more wakefulness inducers of the plurality of wakefulness inducers and actuates the one or more wakefulness inducers.

21. The wakefulness induction control device according to claim 20, wherein the controller stops the wakefulness inducer when a predetermined duration has passed after actuation of the wakefulness inducer.

22. The wakefulness induction control device according to claim 21, wherein the controller changes the predetermined duration in accordance with a current time.

23. The wakefulness induction control device according to claim 21, wherein the controller changes the predetermined duration in accordance with a number of times the wakefulness inducer has been actuated.

24. The wakefulness induction control device according to claim 21, wherein the controller changes the predetermined duration in accordance with a day's total driving duration of the person driving the vehicle.

25. The wakefulness induction control device according to claim 21, wherein the controller stops each of the plurality of wakefulness inducers when the predetermined duration set differently for each of the plurality of wakefulness inducers has passed after actuation of the plurality of wakefulness inducers.

26. The wakefulness induction control device according to claim 25, wherein the controller actuates one or more wakefulness inducers of the plurality of wakefulness inducers, stops the one or more wakefulness inducers, one by one, when the predetermined duration set differently for each of the plurality of wakefulness inducers has passed, and further actuates one or more wakefulness inducers of the plurality of wakefulness inducers that are different from the one or more wakefulness inducers that have been stopped.

27. The wakefulness induction control device according to claim 25, wherein the controller selects one or more wakefulness inducers of the plurality of wakefulness inducers in accordance with a current time and actuates the one or more wakefulness inducers.

28. The wakefulness induction control device according to claim 25, wherein the controller selects one or more wakefulness inducers of the plurality of wakefulness inducers in accordance with a season and actuates the one or more wakefulness inducers.

29. The wakefulness induction control device according to claim 20, wherein the controller determines an accustomedness level indicating a level of accustomedness of the person to the wakefulness inducer and changes a method of actuating the wakefulness inducer based on the accustomedness level determined of the person.

30. A wakefulness induction system, comprising:
the wakefulness induction control device according to claim 20; and
the wakefulness inducer.

31. A wakefulness induction control device, comprising:
a sleepiness detector that detects a sleepiness level indicating a degree of sleepiness of a person and
a controller that actuates a wakefulness inducer that induces wakefulness in the person when the sleepiness level detected by the sleepiness detector meets a predetermined reference;
wherein the wakefulness induction control device is connected to a plurality of the wakefulness inducers that differ in a wakefulness inducing method of inducing wakefulness in the person; and a storage that stores, for each of the plurality of wakefulness inducers, an amount of change in the sleepiness level of the person in a direction of increasing wakefulness of the person, and
wherein the controller actuates one or more wakefulness inducers including a wakefulness inducer of which the amount of change stored in the storage is largest.

32. The wakefulness induction control device according to claim 31, wherein the controller stops the wakefulness inducer when a predetermined duration has passed after actuation of the wakefulness inducer.

33. The wakefulness induction control device according to claim 32, wherein the controller changes the predetermined duration in accordance with a current time.

34. The wakefulness induction control device according to claim 32, wherein the controller changes the predetermined duration in accordance with a number of times the wakefulness inducer has been actuated.

35. The wakefulness induction control device according to claim 32, wherein the controller changes the predetermined duration in accordance with a day's total driving duration of the person driving the vehicle.

36. The wakefulness induction control device according to claim 32, wherein the controller stops each of the plurality of wakefulness inducers when the predetermined duration set differently for each of the plurality of wakefulness inducers has passed after actuation of the plurality of wakefulness inducers.

37. The wakefulness induction control device according to claim 36, wherein the controller actuates one or more wakefulness inducers of the plurality of wakefulness inducers, stops the one or more wakefulness inducers, one by one, when the predetermined duration set differently for each of the plurality of wakefulness inducers has passed, and further actuates one or more wakefulness inducers of the plurality of wakefulness inducers that are different from the one or more wakefulness inducers that have been stopped.

38. The wakefulness induction control device according to claim 36, wherein the controller selects one or more wakefulness inducers of the plurality of wakefulness inducers in accordance with a current time and actuates the one or more wakefulness inducers.

39. The wakefulness induction control device according to claim 36, wherein the controller selects one or more wakefulness inducers of the plurality of wakefulness inducers in accordance with a season and actuates the one or more wakefulness inducers.

40. The wakefulness induction control device according to claim 31, wherein the controller determines an accustomedness level indicating a level of accustomedness of the person to the wakefulness inducer and changes a method of actuating the wakefulness inducer based on the accustomedness level determined of the person.

41. A wakefulness induction system, comprising:
the wakefulness induction control device according to claim 31; and
the wakefulness inducer.

42. A wakefulness induction control device, comprising:
a sleepiness detector that detects a sleepiness level indicating a degree of sleepiness of a person; and
a controller that actuates a wakefulness inducer that induces wakefulness in the person when the sleepiness level detected by the sleepiness detector meets a predetermined reference, and stops the wakefulness inducer when a predetermined duration has passed after actuation of the wakefulness inducer;
wherein the controller changes the predetermined duration in accordance with a day's total driving duration a vehicle is driven.

43. The wakefulness induction control device according to claim 42, wherein the controller changes the predetermined duration in accordance with a current time.

44. The wakefulness induction control device according to claim 42, wherein the controller changes the predetermined duration in accordance with a number of times the wakefulness inducer has been actuated.

45. The wakefulness induction control device according to claim 42, wherein the wakefulness induction control device is connected to a plurality of the wakefulness inducers that differ in a wakefulness inducing method of inducing wakefulness in the person, and the controller stops each of the plurality of wakefulness inducers when the predetermined duration set differently for each of the plurality of wakefulness inducers has passed after actuation of the plurality of wakefulness inducers.

46. The wakefulness induction control device according to claim 45, wherein the controller actuates one or more wakefulness inducers of the plurality of wakefulness inducers, stops the one or more wakefulness inducers, one by one, when the predetermined duration set differently for each of the plurality of wakefulness inducers has passed, and further actuates one or more wakefulness inducers of the plurality of wakefulness inducers that are different from the one or more wakefulness inducers that have been stopped.

47. The wakefulness induction control device according to claim 45, wherein the controller selects one or more wakefulness inducers of the plurality of wakefulness inducers in accordance with a current time and actuates the one or more wakefulness inducers.

48. The wakefulness induction control device according to claim 45, wherein the controller selects one or more wakefulness inducers of the plurality of wakefulness inducers in accordance with a season and actuates the one or more wakefulness inducers.

49. The wakefulness induction control device according to claim 42, wherein the controller determines an accustomedness level indicating a level of accustomedness of the person to the wakefulness inducer and changes a method of actuating the wakefulness inducer based on the accustomedness level determined of the person.

50. A wakefulness induction system, comprising:
the wakefulness induction control device according to claim 42; and
the wakefulness inducer.

51. A wakefulness induction control device, comprising:
a sleepiness detector that detects a sleepiness level indicating a degree of sleepiness of a person and a controller that actuates a wakefulness inducer that induces wakefulness in the person when the sleepiness level detected by the sleepiness detector meets a predetermined reference and change a method of actuating the wakefulness inducer based on a duration a vehicle is driven.

52. The wakefulness induction control device according to claim 51, wherein the controller stops the wakefulness inducer when a predetermined duration has passed after actuation of the wakefulness inducer.

53. The wakefulness induction control device according to claim 52, wherein the controller changes the predetermined duration in accordance with a day's total driving duration the vehicle is driven.

54. The wakefulness induction control device according to claim 52, wherein the wakefulness induction control device is connected to a plurality of the wakefulness inducers that differ in a wakefulness inducing method of inducing wakefulness in the person, and the controller stops each of the plurality of wakefulness inducers when the predetermined duration set differently for each of the plurality of wakefulness inducers has passed after actuation of the plurality of wakefulness inducers.

55. The wakefulness induction control device according to claim 54, wherein the controller selects one or more wakefulness inducers of the plurality of wakefulness inducers in accordance with a current time and actuates the one or more wakefulness inducers.

56. The wakefulness induction control device according to claim 54, wherein the controller selects one or more wakefulness inducers of the plurality of wakefulness inducers in accordance with a season and actuates the one or more wakefulness inducers.

57. The wakefulness induction control device according to claim 54, wherein the controller randomly selects one or more wakefulness inducers of the plurality of wakefulness inducers and actuates the one or more wakefulness inducers.

58. The wakefulness induction control device according to claim 54, wherein the controller selects one or more wakefulness inducers of the plurality of wakefulness inducers in accordance with an attribute of the person and actuates the one or more wakefulness inducers.

59. The wakefulness induction control device according to claim 51, further comprising:
a storage that stores, for each of the plurality of wakefulness inducers, an amount of change in the sleepiness level of the person in a direction of increasing wakefulness of the person with respect to the predetermined duration,
wherein the controller actuates one or more wakefulness inducers including a wakefulness inducer of which the amount of change stored in the storage is largest.

60. The wakefulness induction control device according to claim 51, wherein the controller determines an accustomedness level indicating a level of accustomedness of the person to the wakefulness inducer and changes a method of actuating the wakefulness inducer based on the accustomedness level determined of the person.

* * * * *